(12) United States Patent
Hashimoto et al.

(10) Patent No.: US 12,002,271 B2
(45) Date of Patent: Jun. 4, 2024

(54) IDENTIFICATION DEVICE, SCANNER SYSTEM, AND IDENTIFICATION METHOD

(71) Applicant: J. MORITA MFG. CORP., Kyoto (JP)

(72) Inventors: Manabu Hashimoto, Nagoya (JP); Ryosuke Kaji, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 413 days.

(21) Appl. No.: 17/415,263

(22) PCT Filed: Dec. 12, 2019

(86) PCT No.: PCT/JP2019/048650
§ 371 (c)(1),
(2) Date: Jun. 17, 2021

(87) PCT Pub. No.: WO2020/129799
PCT Pub. Date: Jun. 25, 2020

(65) Prior Publication Data
US 2022/0058372 A1      Feb. 24, 2022

(30) Foreign Application Priority Data

Dec. 17, 2018   (JP) .................................. 2018-235628

(51) Int. Cl.
*G16H 30/40*       (2018.01)
*A61B 1/24*        (2006.01)
(Continued)

(52) U.S. Cl.
CPC ................ *G06V 20/64* (2022.01); *A61B 1/24* (2013.01); *A61B 5/0062* (2013.01);
(Continued)

(58) Field of Classification Search
CPC ........................................... G06T 2207/30036
See application file for complete search history.

(56) References Cited

U.S. PATENT DOCUMENTS 6,885,464 B1    4/2005  Pfeiffer et al.
7,605,817 B2    10/2009 Zhang et al.
(Continued)

FOREIGN PATENT DOCUMENTS

CN      104867148 A     8/2015
CN      106228550 A     12/2016
(Continued)

OTHER PUBLICATIONS

Notification to Go Through Formalities of Registration issued in counterpart Japanese Patent Application No. 2019800828164 dated Apr. 24, 2023 (2 pages).
(Continued)

*Primary Examiner* — Di Xiao
(74) *Attorney, Agent, or Firm* — Osha Bergman Watanabe & Burton LLP

(57) ABSTRACT

An identification device includes: an input unit that receives three-dimensional data including data of a tooth; an identification unit that identifies a type of the tooth based on the three-dimensional data including a feature of the tooth received by the input unit and an estimation model including a neural network; and an output unit that outputs an identification result obtained by the identification unit.

17 Claims, 18 Drawing Sheets

(51) Int. Cl.
    *A61B 5/00* (2006.01)
    *G06F 18/214* (2023.01)
    *G06V 10/40* (2022.01)
    *G06V 20/64* (2022.01)
    *G16H 50/50* (2018.01)

(52) U.S. Cl.
    CPC .......... *A61B 5/0088* (2013.01); *G06F 18/214* (2023.01); *G06V 10/40* (2022.01); *G16H 30/40* (2018.01); *G16H 50/50* (2018.01); *G06V 2201/03* (2022.01)

(56) References Cited

U.S. PATENT DOCUMENTS

| | | | |
|---|---|---|---|
| 7,956,862 | B2 | 6/2011 | Zhang et al. |
| 2008/0172386 | A1 | 7/2008 | Ammar et al. |
| 2014/0028010 | A1* | 1/2014 | Trava ............... G16H 50/70 283/67 |
| 2017/0071713 | A1* | 3/2017 | Nakai ............... A61B 6/5247 |
| 2017/0169562 | A1 | 6/2017 | Somasundaram et al. |
| 2017/0340419 | A1 | 11/2017 | Ohtake et al. |
| 2017/0367789 | A1 | 12/2017 | Fujiwara et al. |
| 2018/0028294 | A1* | 2/2018 | Azernikov ........ G06F 18/24143 |
| 2018/0061054 | A1 | 3/2018 | Abraham et al. |
| 2018/0085201 | A1 | 3/2018 | Wu et al. |
| 2018/0284727 | A1 | 10/2018 | Cramer et al. |
| 2018/0360567 | A1* | 12/2018 | Xue ............... A61C 7/002 |
| 2018/0368954 | A1* | 12/2018 | Katzman ............ A61C 9/0006 |
| 2019/0343601 | A1* | 11/2019 | Roschin ............ A61C 7/002 |
| 2019/0370965 | A1* | 12/2019 | Lay ............... G06N 20/00 |
| 2020/0320685 | A1* | 10/2020 | Anssari Moin ........... G06T 7/11 |
| 2021/0290070 | A1* | 9/2021 | Cohen ............... A46B 13/02 |
| 2022/0165388 | A1* | 5/2022 | Chernov ............ A61B 5/004 |

FOREIGN PATENT DOCUMENTS

| | | |
|---|---|---|
| CN | 106504331 A | 3/2017 |
| CN | 107440810 A | 12/2017 |
| CN | 108389207 A | 8/2018 |
| CN | 108491850 A | 9/2018 |
| JP | 2000-074635 A | 3/2000 |
| JP | 2017-213060 A | 12/2017 |
| JP | 2018-063707 A | 4/2018 |
| WO | 2016/143022 A1 | 9/2016 |
| WO | 2018/167530 A1 | 9/2018 |

OTHER PUBLICATIONS

Offie Action issued in counterpart Japanese Patent Application No. 2019800828164 dated Apr. 24, 2023 (4 pages).
Office Action issued in the counterpart Japanese Patent Application No. 2019-190003, dated Jan. 26, 2021 (7 pages).
S. Raith et al. "Artificial Neural Networks as a powerful numerical tool to classify specific features of a tooth based on 3D scan data" Computers in Biology and Medicine, vol. 80; New York, NY, USA; Nov. 27, 2016 (12 pages).
X. Xu et al. "3D Tooth Segmentation and Labeling using Deep Convolutional Neural Networks" IEEE Transactions on Visualization and Computer Graphics; May 22, 2018 (13 pages).
Extended European Search Report issued in European Application No. 19901206.3, dated Aug. 1, 2022 (8 pages).
Notification to Go Through Formalities of Registration issued in counterpart Chinese Patent Application No. 2019800828164 dated Apr. 24, 2023 (2 pages).
Offie Action issued in counterpart Chinese Patent Application No. 2019800828164 dated Apr. 24, 2023 (4 pages).
Office Action in counterpart Chinese Patent Application No. 201980082816.4 dated Dec. 30, 2021 (21 pages).
International Search Report issued in Application No. PCT/JP2019/048650, dated Mar. 3, 2020 (5 pages).
Written Opinion issued in International Application No. PCT/JP2019/048650, dated Mar. 3, 2020 (5 pages).

* cited by examiner

FIG.7

| DATA ACQUISITION SITE | IMAGING DIRECTION | | |
|---|---|---|---|
| INCISOR IN UPPER JAW | PLANE ON UPPER LIP SIDE | PLANE ON PALATE SIDE | PLANE ON INCISAL EDGE SIDE |
| CANINE IN UPPER JAW | PLANE ON BUCCAL SIDE | PLANE ON PALATE SIDE | PLANE OF OCCLUSION |
| MOLAR IN UPPER JAW | PLANE ON BUCCAL SIDE | PLANE ON PALATE SIDE | PLANE OF OCCLUSION |
| INCISOR IN LOWER JAW | PLANE ON LOWER LIP SIDE | PLANE ON TONGUE SIDE | PLANE ON INCISAL EDGE SIDE |
| CANINE IN LOWER JAW | PLANE ON BUCCAL SIDE | PLANE ON TONGUE SIDE | PLANE OF OCCLUSION |
| MOLAR IN LOWER JAW | PLANE ON BUCCAL SIDE | PLANE ON TONGUE SIDE | PLANE OF OCCLUSION |

FIG.17

MODIFICATION

| LEARNING DATA SET | | | | | |
|---|---|---|---|---|---|
| POSITION INFORMATION | | | NORMAL LINE INFORMATION | COLOR INFORMATION (BEFORE COLOR-CODING) | COLOR INFORMATION (AFTER COLOR-CODING) |
| X | Y | Z | N | RGB | RGB |
| ... | ... | ... | ... | 239239239 | 255000000 |
| ... | ... | ... | ... | 236236236 | 255000000 |
| ... | ... | ... | ... | 233233233 | 255000000 |
| ... | ... | ... | ... | 229229229 | 255000000 |
| ... | ... | ... | ... | 223223223 | 255000000 |
| ○ | × | × | ○ | × | ○ |
| × | ○ | ○ | × | ○ | × |
| ○ | × | × | ○ | × | ○ |
| ... | ... | ... | ... | 222222222 | 000255000 |
| ... | ... | ... | ... | 227227227 | 000255000 |
| ... | ... | ... | ... | 232232432 | 000255000 |
| ... | ... | ... | ... | 239239239 | 000255000 |
| ... | ... | ... | ... | 241241241 | 000255000 |
| ○ | × | × | ○ | × | ○ |
| × | ○ | ○ | × | ○ | × |
| ○ | × | × | ○ | × | ○ |
| ... | ... | ... | ... | 233253243 | 000000255 |
| ... | ... | ... | ... | 229239221 | 000000255 |
| ... | ... | ... | ... | 223243223 | 000000255 |
| ... | ... | ... | ... | 222423213 | 000000255 |
| ... | ... | ... | ... | 227114225 | 000000255 |
| ○ | × | × | ○ | × | ○ |
| × | ○ | ○ | × | ○ | × |
| ○ | × | × | ○ | × | ○ |

IDENTIFICATION DEVICE, SCANNER SYSTEM, AND IDENTIFICATION METHOD

TECHNICAL FIELD

The present invention relates to an identification device, a scanner system including the identification device, and an identification method.

BACKGROUND ART

In the dental field, a three-dimensional scanner has conventionally been known that incorporates a three-dimensional camera for acquiring a three-dimensional shape of a tooth in order to digitally design a prosthesis or the like on a computer. For example, PTL 1 discloses a technique for imaging a tooth using a three-dimensional camera for recording the shape of the tooth. An operator such as a dentist uses the three-dimensional camera disclosed in PTL 1 and thereby can record a three-dimensional shape of a tooth as a target to be imaged, and also, can identify a type of the tooth based on his/her knowledge while checking the three-dimensional image showing the recorded three-dimensional shape of the tooth.

CITATION LIST

Patent Literature

PTL 1: Japanese Patent Laying-Open No. 2000-74635

SUMMARY OF INVENTION

Technical Problem

As described above, operators have conventionally identified a type of a tooth from their knowledge based on a three-dimensional image including the tooth acquired by a three-dimensional camera. However, since the levels of knowledge vary for each operator, there has been a problem that the accuracy of the identification result varied depending on the levels of the operator's knowledge. For example, the accuracy is not particularly high for identification between teeth having similar shapes, such as between a central incisor and a lateral incisor, between a canine and a first premolar, between a first premolar and a second premolar, between a second premolar and a first molar, and between a first molar and a second molar.

The present invention has been made in order to solve the above-described problem, and an object of the present invention is to provide an identification device capable of accurately identifying a type of a tooth, a scanner system including the identification device, and an identification method.

Solution to Problem

According to the present invention, an identification device that identifies a type of a tooth is provided. The identification device includes: an input unit that receives three-dimensional data including data of the tooth; an identification unit that identifies a type of the tooth based on the three-dimensional data including a feature of the tooth received by the input unit and an estimation model including a neural network; and an output unit that outputs an identification result obtained by the identification unit.

According to the present invention, a scanner system that acquires shape information of a tooth is provided. The scanner system includes: a three-dimensional scanner that acquires three-dimensional data including data of the tooth using a three-dimensional camera; and an identification device that identifies a type of the tooth based on the three-dimensional data including a feature of the tooth acquired by the three-dimensional scanner. The identification device includes: an input unit that receives the three-dimensional data; an identification unit that identifies a type of the tooth based on the three-dimensional data including a feature of the tooth received by the input unit and an estimation model including a neural network; and an output unit that outputs an identification result obtained by the identification unit.

According to the present invention, an identification method of identifying a type of a tooth is provided. The identification method includes: receiving three-dimensional data including data of the tooth; identifying a type of the tooth based on the three-dimensional data including a feature of the tooth and an estimation model including a neural network; and outputting an identification result obtained by the identifying a type of the tooth.

Advantageous Effects of Invention

According to the present invention, a type of a tooth can be accurately identified based on three-dimensional data including data of the tooth.

BRIEF DESCRIPTION OF DRAWINGS

FIG. 7 is a schematic diagram showing examples of teeth to be identified in the identification process according to the present embodiment.

FIG. 17 is a schematic diagram for illustrating an example of a learning data set according to the modification.

DESCRIPTION OF EMBODIMENTS

Figure 1:
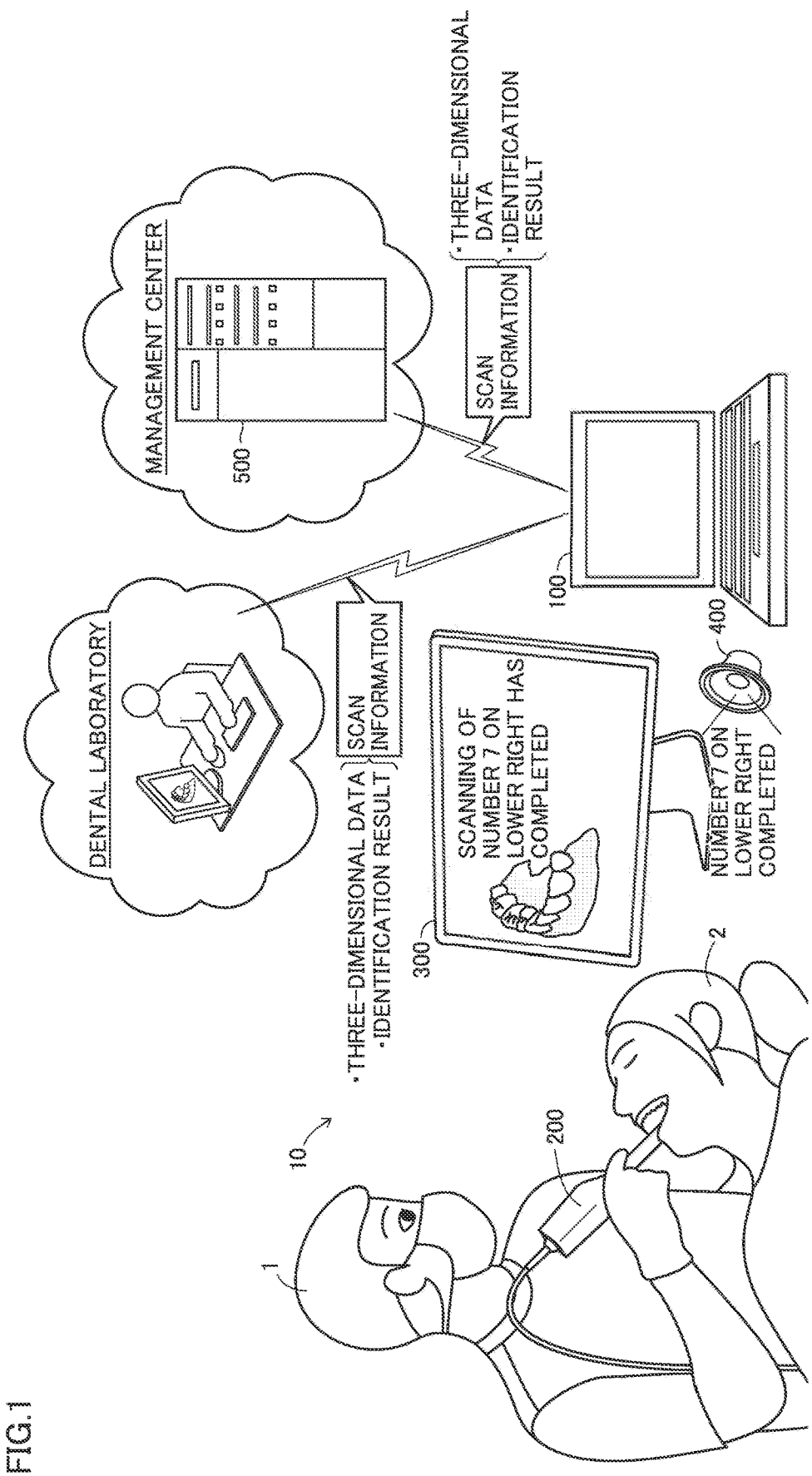
FIG. 1 is a schematic diagram showing an application example of an identification device according to the present embodiment.

Embodiments of the present invention will be hereinafter described in detail with reference to the accompanying drawings, in which the same or corresponding components are denoted by the same reference characters, and the description thereof will not be repeated.

Application Example

Figure 2:
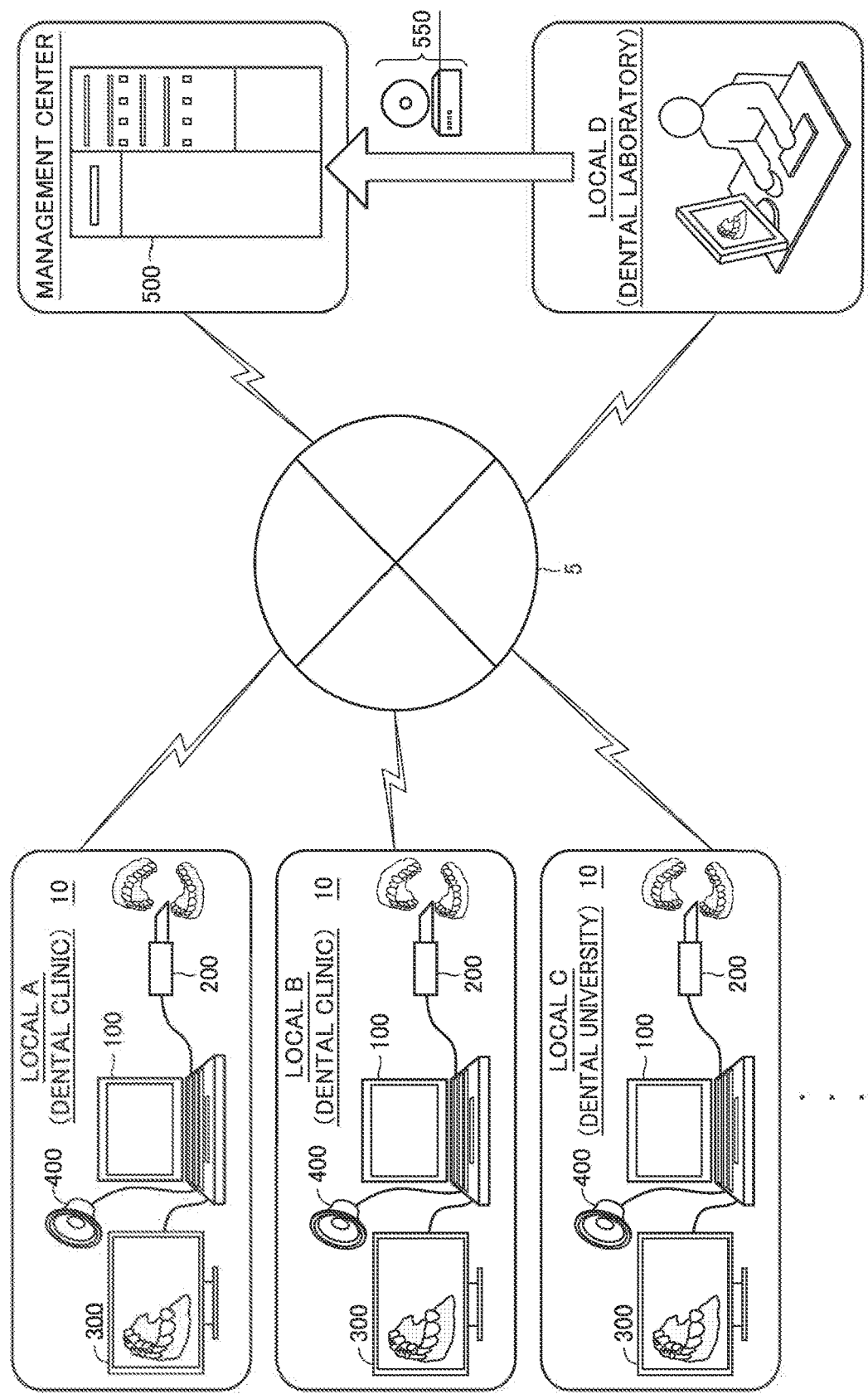
FIG. 2 is a schematic diagram showing the entire configuration of a system according to the present embodiment.

An application example of an identification device 100 according to the present embodiment will be hereinafter described with reference to FIGS. 1 and 2. FIG. 1 is a schematic diagram showing an application example of identification device 100 according to the present embodiment. FIG. 2 is a schematic diagram showing the entire configuration of a system according to the present embodiment.

As shown in FIG. 1, a user 1 uses a scanner system 10 and thereby can acquire data of a three-dimensional shape (hereinafter also referred to as "three-dimensional data") including data of teeth of a subject 2. The "user" may be any person who uses scanner system 10, for example, an operator such as a dentist, a dental assistant, a teacher or a student of dental university, a dental engineer, an engineer of a manufacturer, an operator in a manufacturing factory, and the like. The "subject" may be any person as a target of scanner system 10, such as a patient in a dental clinic or a subject in a dental university.

Scanner system 10 according to the present embodiment includes a three-dimensional scanner 200, an identification device 100, a display 300, and a speaker 400. Three-dimensional scanner 200 acquires three-dimensional data to be scanned by a built-in three-dimensional camera. Specifically, three-dimensional scanner 200 scans the inside of an oral cavity to acquire, as three-dimensional data, position information (coordinates of each of axes in the vertical direction, the horizontal direction, and the height direction) at each of a plurality of points forming a tooth to be scanned, for which an optical sensor or the like is used. Identification device 100 generates a three-dimensional image based on the three-dimensional data acquired by three-dimensional scanner 200, and causes display 300 to show the generated three-dimensional image.

For example, in order to digitally design a prosthesis or the like on a computer for filling a defect portion in a tooth of subject 2, user 1 uses three-dimensional scanner 200 to image the inside of the oral cavity of subject 2 to thereby acquire three-dimensional data of the inside of the oral cavity including teeth. Each time user 1 images the inside of the oral cavity, three-dimensional data is sequentially acquired and then a three-dimensional image of the inside of the oral cavity is shown on display 300. User 1 scans mainly a portion lacking three-dimensional data while checking the three-dimensional image shown on display 300. At this time, based on the three-dimensional image obtained by visualization of the three-dimensional data including data of the teeth acquired by three-dimensional scanner 200, and also from the knowledge of user 1, user 1 identifies a type of the tooth that is being scanned or that has been completely scanned. However, since the level of knowledge is different for each user 1, the accuracy of the identification result may vary depending on the knowledge of user 1.

Thus, scanner system 10 according to the present embodiment is configured to perform a process of automatically identifying a type of a tooth based on the three-dimensional data acquired by three-dimensional scanner 200 with the help of artificial intelligence (AI) included in identification device 100. The process of identifying a type of a tooth by identification device 100 will also be referred to as an "identification process".

A "type of a tooth" means a type of each of teeth such as: a central incisor, a lateral incisor, a canine, a first premolar, a second premolar, a first molar, a second molar, and a third molar on the right side in an upper jaw; a central incisor, a lateral incisor, a canine, a first premolar, a second premolar, a first molar, a second molar, and a third molar on the left side in the upper jaw; a central incisor, a lateral incisor, a canine, a first premolar, a second premolar, a first molar, a second molar, and a third molar on the right side in a lower jaw; and a central incisor, a lateral incisor, a canine, a first premolar, a second premolar, a first molar, a second molar, and a third molar on the left side in the lower jaw.

Specifically, when user 1 scans teeth inside the oral cavity of subject 2 using three-dimensional scanner 200, three-dimensional data including data of teeth is input into identification device 100. Identification device 100 performs an identification process of identifying a type of a tooth based on the input three-dimensional data including a feature of the tooth and an estimation model including a neural network.

The "estimation model" includes a neural network and a parameter used by the neural network, and is optimized (adjusted) when this "estimation model" is learned based on: the tooth information corresponding to the type of the tooth associated with the three-dimensional data; and an identification result about the type of the tooth that is obtained using the three-dimensional data. Specifically, when the three-dimensional data including data of a tooth is input, the estimation model extracts a feature of the tooth by the neural network based on the three-dimensional data, and estimates a type of the tooth based on the extracted feature of the tooth. As to the estimation model, based on the comparison between the type of the tooth estimated by the estimation model and the type of the tooth (tooth information) associated with the input three-dimensional data, if the types match with each other, the parameter is not updated, whereas, if the types do not match with each other, the parameter is updated such that the types match with each other, thereby optimizing the parameter. In this way, the estimation model is learned by optimizing the parameter using teacher data including the three-dimensional data as input data and the type of the tooth (tooth information) as correct data.

Such a process of learning the estimation model will also be referred to as a "learning process". The estimation model optimized by the learning process will also be particularly referred to as a "learned model". In other words, in the present embodiment, the estimation model before learning and the learned estimation model will be collectively referred to as an "estimation model", and particularly, the learned estimation model will also be referred to as a "learned model".

The "tooth information" includes names of teeth such as: a central incisor, a lateral incisor, a canine, a first premolar, a second premolar, a first molar, a second molar, and a third molar on the right side in an upper jaw; a central incisor, a lateral incisor, a canine, a first premolar, a second premolar, a first molar, a second molar, and a third molar on the left side in the upper jaw; a central incisor, a lateral incisor, a canine, a first premolar, a second premolar, a first molar, a second molar, and a third molar on the right side in a lower jaw; and a central incisor, a lateral incisor, a canine, a first premolar, a second premolar, a first molar, a second molar, and a third molar on the left side in the lower jaw. Further, the "tooth information" includes numbers assigned to respective teeth (for example, the tooth numbers generally used in the dental field) such as: number 1 assigned to a central incisor, number 2 assigned to a lateral incisor, number 3 assigned to a canine, number 4 assigned to a first premolar, number 5 assigned to a second premolar, number 6 assigned to a first molar, number 7 assigned to a second molar, and number 8 assigned to a third molar. In addition, the "tooth information" may include information of colors assigned to the respective teeth or information of symbols assigned to the respective teeth.

When identification device 100 performs the identification process using the learned model, the identification result is output to display 300 and speaker 400.

Display 300 shows at least one of an image, a character, a numeral, an icon, and a symbol that correspond to the identification result. For example, after three-dimensional scanner 200 completes scanning of the second molar corresponding to number 7 on the right side in the lower jaw, display 300 adopts the identification result about the tooth obtained by identification device 100 to show an image indicating that scanning of the second molar corresponding to number 7 on the right side in the lower jaw has completed, for example, by showing a message such as "Scanning of number 7 on lower right has completed".

Speaker 400 outputs a sound corresponding to the identification result. For example, after three-dimensional scanner 200 completes scanning of the second molar corresponding to number 7 on the right side in the lower jaw, speaker 400 adopts the identification result about the tooth obtained by identification device 100, and outputs a sound indicating that scanning of the second molar corresponding to number 7 on the right side in the lower jaw has completed, for example, by showing a message such as "Number 7 on lower right has completed".

Further, the identification result obtained by identification device 100 is output together with the three-dimensional data used in the identification process, as scan information, to a dental laboratory and server device 500 disposed in a management center.

For example, as shown in FIG. 2, scanner system 10 is disposed in each of a plurality of locals A to C. For example, locals A and B each are a dental clinic. In such a dental clinic, an operator or a dental assistant as user 1 uses scanner system 10 to acquire three-dimensional data including data of teeth of a patient as subject 2. Local C is a dental university, in which a teacher or a student as user 1 acquires three-dimensional data of the inside of the oral cavity of a target as subject 2. The scan information (three-dimensional data, identification result) acquired in each of locals A to C is output through a network 5 to a dental laboratory as a local D and server device 500 disposed in a management center.

In the dental laboratory, based on the scan information acquired from each of locals A to C, a dental engineer or the like creates a prosthesis or the like for filling a defect portion in a tooth of subject 2. In the management center, server device 500 stores an accumulation of the scan information acquired from each of locals A to C, and holds the stored information as big data.

It should be noted that server device 500 does not necessarily have to be disposed in a management center different from a local in which the dental clinic is disposed, but may be disposed in a local. For example, server device 500 may be disposed in any one of locals A to C. Further, a plurality of identification devices 100 may be disposed in one local. Also, server device 500 capable of communicating with the plurality of identification devices 100 may be disposed in this one local. Further, server device 500 may be implemented in the form of a cloud service.

In a dental laboratory, scan information is aggregated from various locations such as locals A to C. Thus, the scan information held in the dental laboratory may be transmitted to the management center through network 5, or may be transmitted to the management center through a removable disk 550 such as a compact disc (CD) and a universal serial bus (USB) memory.

In addition, the scan information may be sent to the management center also from each of locals A to C through removable disk 550 without through network 5. Further, the scan information may be exchanged also among locals A to C through network 5 or removable disk 550.

Identification device 100 in each of locals A to C holds an estimation model, and uses the holding estimation model to identify a type of a tooth during the identification process. Identification devices 100 in locals A to C learn their respective estimation models by their respective learning processes to generate learned models. Further, in the present embodiment, server device 500 also holds an estimation model. Server device 500 learns the estimation model by the learning process performed using the scan information acquired from identification device 100 in each of locals A to C and from the dental laboratory, to thereby generate a learned model and then distribute the learned model to identification device 100 in each of locals A to C. In the present embodiment, each of identification devices 100 in locals A to C and server device 500 performs the learning process, but only each of identification devices 100 in locals A to C may perform the learning process, or only server device 500 may perform the learning process. In the case where only server device 500 performs the learning process, the estimation model (learned model) held by identification device 100 in each of locals A to C is shared among identification devices 100 in locals A to C.

Further, server device 500 may have a function of the identification process in identification device 100. For example, each of locals A to C may transmit the acquired three-dimensional data to server device 500. Then, based on the three-dimensional data received from each of local areas A to C, server device 500 may calculate the identification result about the type of the tooth in each three-dimensional data. Then, server device 500 may transmit the identification results to their respective locals A to C. Then, locals A to C may output the identification results received from server device 500 to their respective displays or the like. In this way, each of locals A to C and server device 500 may be configured in the form of a cloud service. In this way, server device 500 only has to hold the estimation model (learned model), and thereby, each of locals A to C can obtain the identification result without having to hold the estimation model (learned model).

In this way, according to scanner system 10 of the present embodiment, the AI included in identification device 100 is used to automatically identify a type of a tooth based on the three-dimensional data acquired by three-dimensional scanner 200. By using the AI, the feature of a tooth obtained from the knowledge of user 1 can be found. Further, the feature of a tooth that cannot be extracted by user 1 can also be found. Thereby, user 1 can accurately identify a type of a tooth without relying on his/her own knowledge.

[Hardware Configuration of Identification Device]

Figure 3:
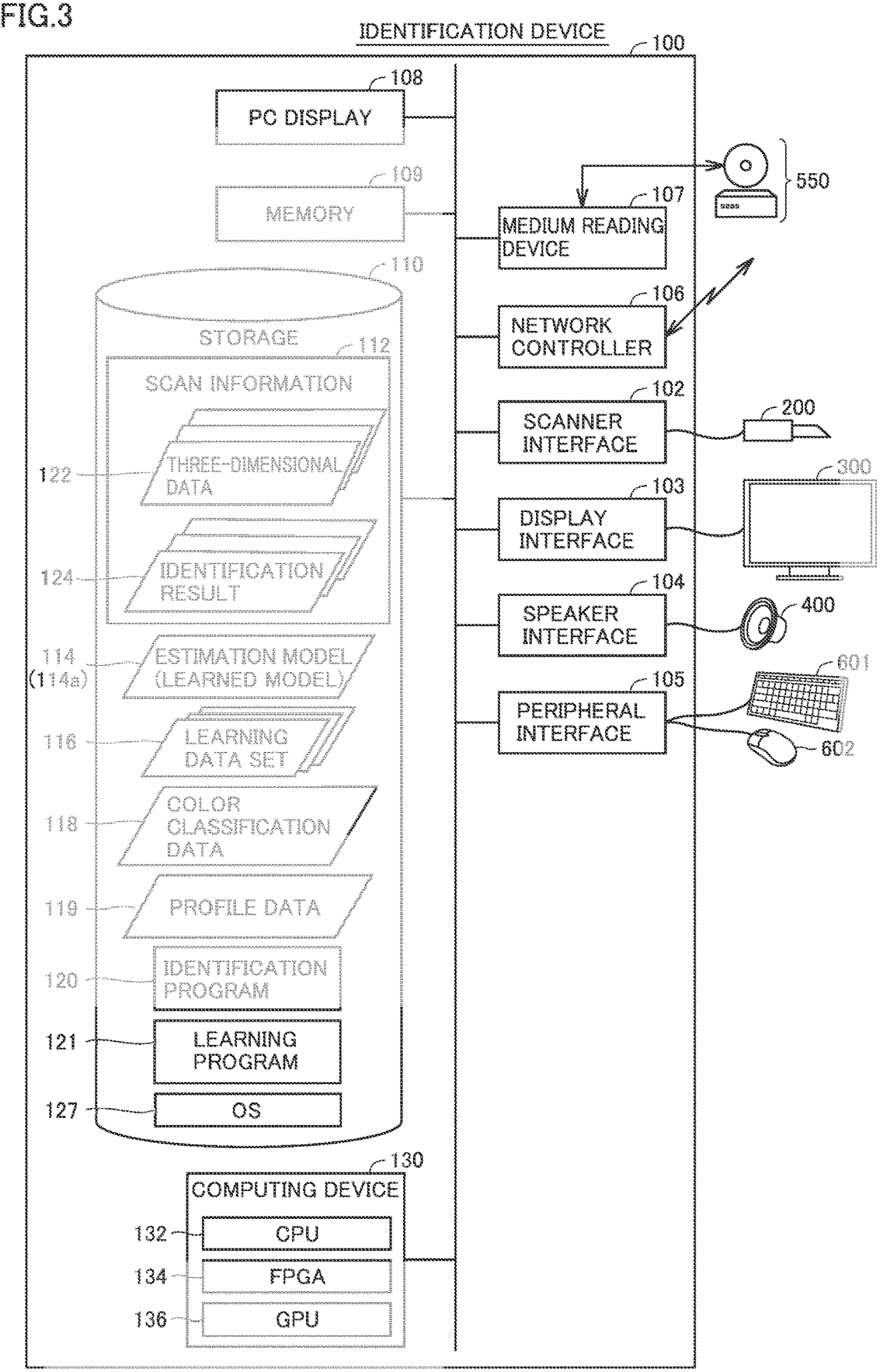
FIG. 3 is a schematic diagram showing a hardware configuration of the identification device according to the present embodiment.

An example of a hardware configuration of identification device 100 according to the present embodiment will be hereinafter described with reference to FIG. 3. FIG. 3 is a schematic diagram showing a hardware configuration of identification device 100 according to the present embodiment. Identification device 100 may be implemented, for example, by a general-purpose computer or a computer dedicated to scanner system 10.

As shown in FIG. 3, identification device 100 includes, as main hardware elements, a scanner interface 102, a display interface 103, a speaker interface 104, a peripheral interface 105, a network controller 106, a medium reading device 107, a PC display 108, a memory 109, a storage 110, and a computing device 130.

Scanner interface 102, which is an interface for connecting three-dimensional scanner 200, implements input/output of data between identification device 100 and three-dimensional scanner 200.

Display interface 103, which is an interface for connecting display 300, implements input/output of data between identification device 100 and display 300. Display 300 is configured, for example, by a liquid crystal display (LCD), an organic electroluminescence (ELD) display or the like.

Speaker interface 104, which is an interface for connecting speaker 400, implements input/output of data between identification device 100 and speaker 400.

Peripheral interface 105, which is an interface for connecting peripheral devices such as a keyboard 601 and a mouse 602, implements input/output of data between identification device 100 and each peripheral device.

Network controller 106 transmits and receives data through network 5 to and from each of: a device disposed in the dental laboratory; server device 500 disposed in the management center; and other identification devices 100 disposed in other locals. Network controller 106 supports optional communication schemes such as Ethernet (registered trademark), a wireless local area network (LAN), or Bluetooth (registered trademark).

Medium reading device 107 reads various pieces of data such as scan information stored in removable disk 550.

PC display 108 is a display dedicated to identification device 100. PC display 108 is configured by an LCD or an organic EL display, for example. In the present embodiment, PC display 108 is provided separately from display 300 but may be integrated with display 300.

Memory 109 provides a storage area in which program codes, work memory, and the like are temporarily stored when computing device 130 executes an optional program. Memory 109 is configured by a volatile memory device such as a dynamic random access memory (DRAM) or a static random access memory (SRAM), for example.

Storage 110 provides a storage area in which various pieces of data required for the identification process, the learning process, and the like are stored. Storage 110 is configured by a non-volatile memory device such as a hard disk or a solid state drive (SSD), for example.

Storage 110 stores scan information 112, an estimation model 114 (a learned model 114a), a learning data set 116, color classification data 118, profile data 119, an identification program 120, a learning program 121, and an operating system (OS) 127.

Scan information 112 includes three-dimensional data 122 acquired by three-dimensional scanner 200, and an identification result 124 obtained by the identification process performed based on three-dimensional data 122. Identification result 124 is associated with three-dimensional data 122 used in the identification process and is stored in storage 110. Learning data set 116 is a group of learning data used for the learning process of estimation model 114. Color classification data 118 is data used for generation of learning data set 116 and the learning process. Profile data 119 is attribute information related to subject 2 and includes a summary of profiles about subject 2 (for example, information on medical charts) such as an age, a gender, a race, a height, a weight, and a place of residence. Identification program 120 is a program for performing the identification process. Learning program 121 is a program for performing the learning process of estimation model 114, and also includes a program for performing the identification process.

Computing device 130 is a computing entity that executes various programs to thereby perform various processes such as an identification process and a learning process. Computing device 130 is also one example of a computer. Computing device 130 is configured, for example, by a central processing unit (CPU) 132, a field-programmable gate array (FPGA) 134, a graphics processing unit (GPU) 136, and the like. Computing device 130 may be configured by at least one of CPU 132, FPGA 134, and GPU 136, or may be configured by: CPU 132 and FPGA 134; FPGA 134 and GPU 136; CPU 132 and GPU 136; or CPU 132, FPGA 134, and GPU 136. Computing device 130 may also be referred to as processing circuitry.

[Hardware Configuration of Server Device]

Figure 4:
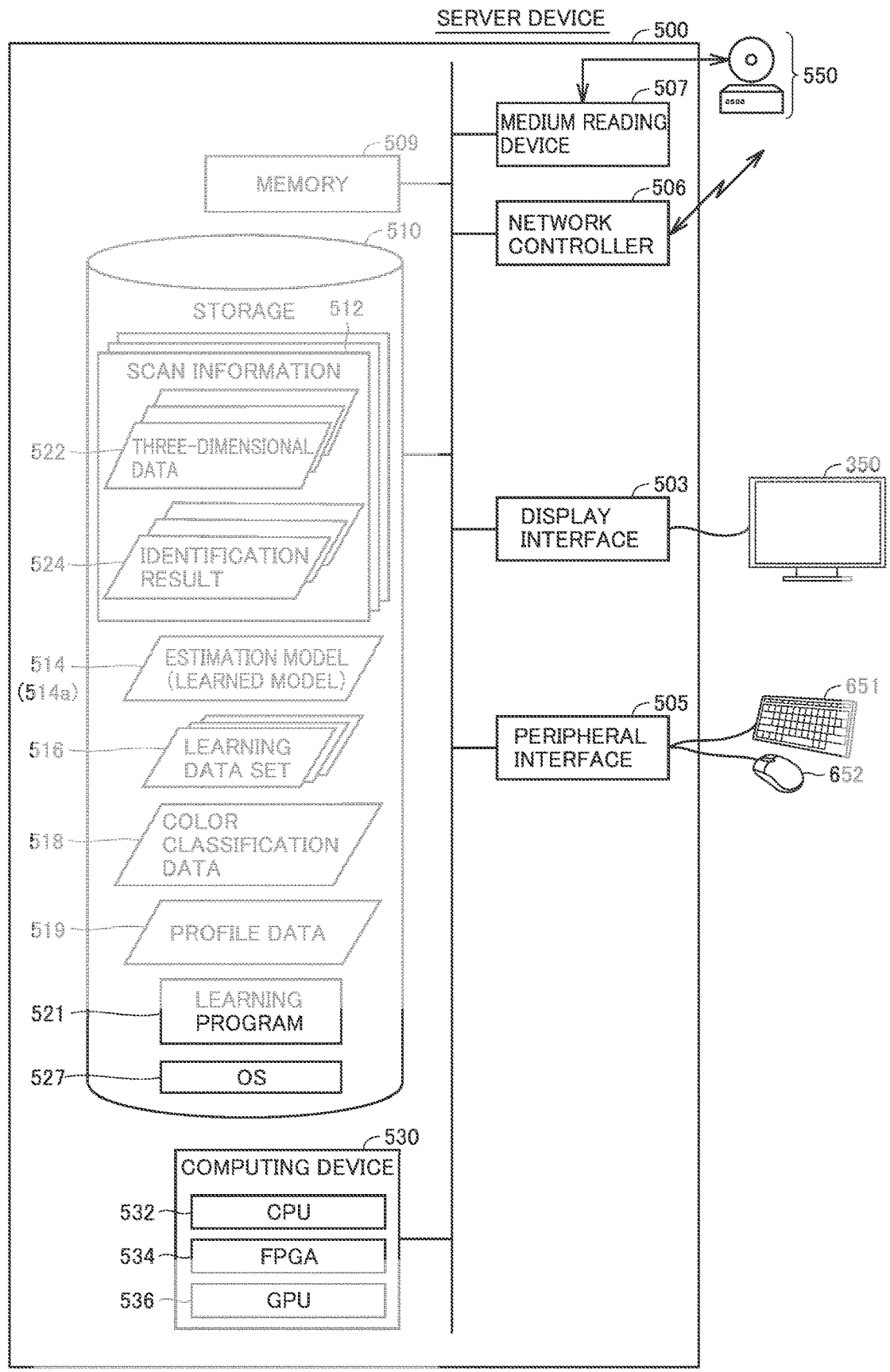
FIG. 4 is a schematic diagram showing a hardware configuration of a server device according to the present embodiment.

An example of a hardware configuration of server device 500 according to the present embodiment will be hereinafter described with reference to FIG. 4. FIG. 4 is a schematic diagram showing a hardware configuration of server device 500 according to the present embodiment. Server device 500 may be implemented, for example, by a general-purpose computer or by a computer dedicated to scanner system 10.

As shown in FIG. 4, server device 500 includes, as main hardware elements, a display interface 503, a peripheral interface 505, a network controller 506, a medium reading device 507, a memory 509, a storage 510, and a computing device 530.

Display interface 503, which is an interface for connecting display 350, implements input/output of data between server device 500 and display 350. Display 350 is configured, for example, by an LCD, an organic ELD display, or the like.

Peripheral interface 505, which is an interface for connecting peripheral devices such as a keyboard 651 and a mouse 652, implements input/output of data between server device 500 and each peripheral device.

Network controller 506 transmits and receives data through network 5 to and from each of identification device 100 disposed in each local and a device disposed in a dental laboratory. Network controller 506 may support optional communication schemes such as Ethernet (registered trademark), a wireless LAN, or Bluetooth (registered trademark).

Medium reading device 507 reads various pieces of data such as scan information stored in removable disk 550.

Memory 509 provides a storage area in which program codes, work memory, and the like are temporarily stored when computing device 530 executes an optional program. Memory 509 is configured, for example, by a volatile memory device such as a DRAM or an SRAM.

Storage 510 provides a storage area in which various pieces of data required for the learning process and the like is stored. Storage 510 is configured, for example, by a non-volatile memory device such as a hard disk or an SSD.

Storage 510 stores scan information 512, an estimation model 514 (a learned model 514a), a learning data set 516, color classification data 518, profile data 519, a learning program 521, and an OS 527.

Scan information 512 includes: three-dimensional data 522 acquired through network 5 from identification device 100 and a dental laboratory disposed in locals; and an identification result 524 obtained by an identification process performed based on three-dimensional data 522. Identification result 524 is associated with three-dimensional data 522 used in the identification process and is stored in storage 510. Learning data set 516 is a group of learning data used for the learning process of estimation model 514. Color classification data 518 is data used for generation of learning data set 516 and the learning process. Profile data 519 is attribute information related to subject 2 and includes a summary of profiles about subject 2 (for example, information on medical charts) such as an age, a gender, a race, a height, a weight, and a place of residence. Learning program 521 is a program for performing the learning process of estimation model 514, and also includes a program for performing the identification process.

In addition, estimation model 514 (learned model 514a) is transmitted to identification device 100 in each local, and thereby, held as estimation model 114 (learned model 114a) by identification device 100.

Computing device 530 is a computing entity that executes various programs to thereby perform various processes such as a learning process. Computing device 530 is also one example of a computer. Computing device 530 is configured, for example, by a CPU 532, an FPGA 534, a GPU 536, and the like. Computing device 530 may be configured by at least one of CPU 532, FPGA 534, and GPU 536, or may be configured by: CPU 532 and FPGA 534; FPGA 534 and GPU 536; CPU 532 and GPU 536; or CPU 532, FPGA 534, and GPU 536. Computing device 530 may also be referred to as processing circuitry.

[Identification Process by Identification Device]

Figure 5:
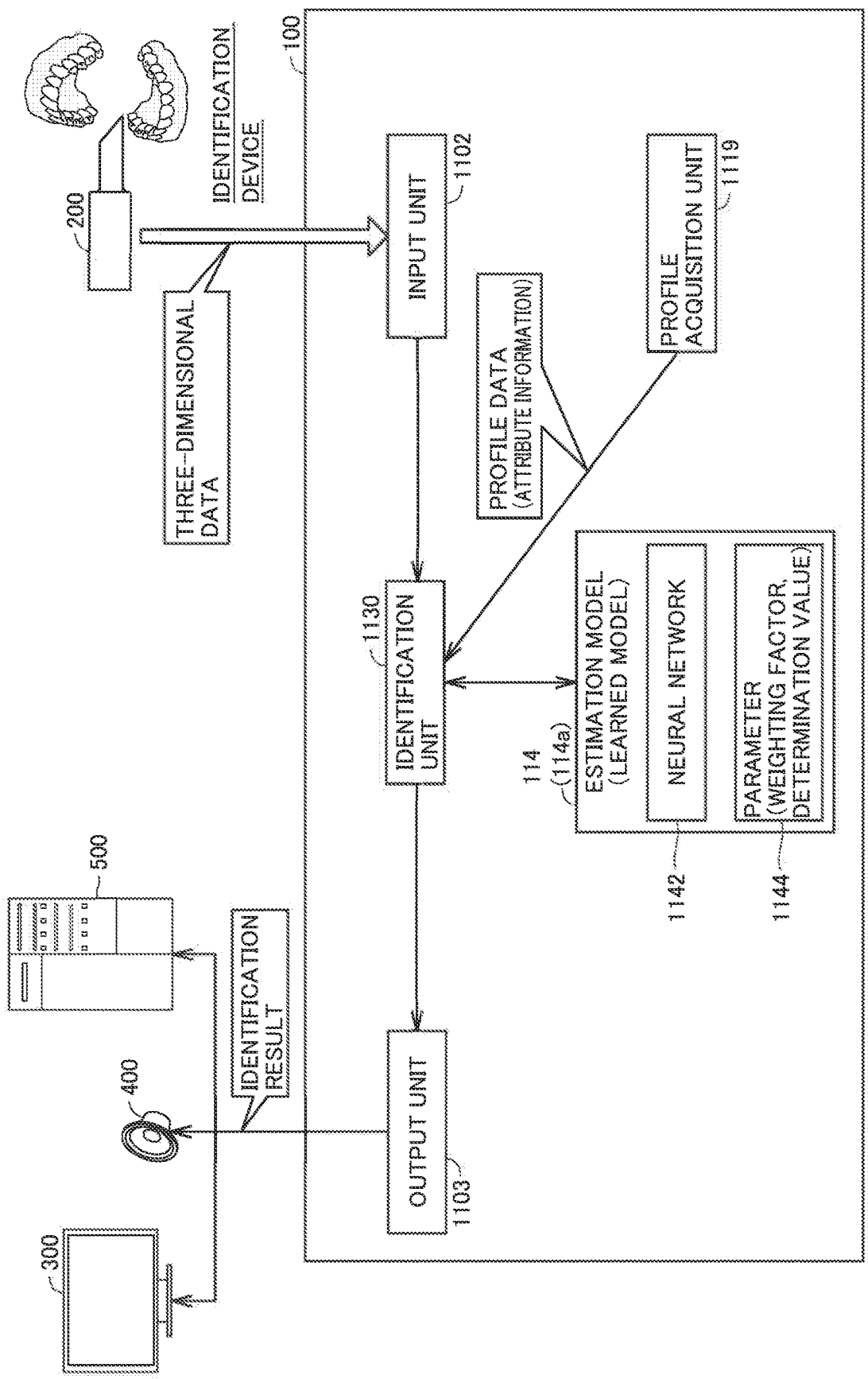
FIG. 5 is a schematic diagram showing a functional configuration of the identification device according to the present embodiment.
Figure 6:
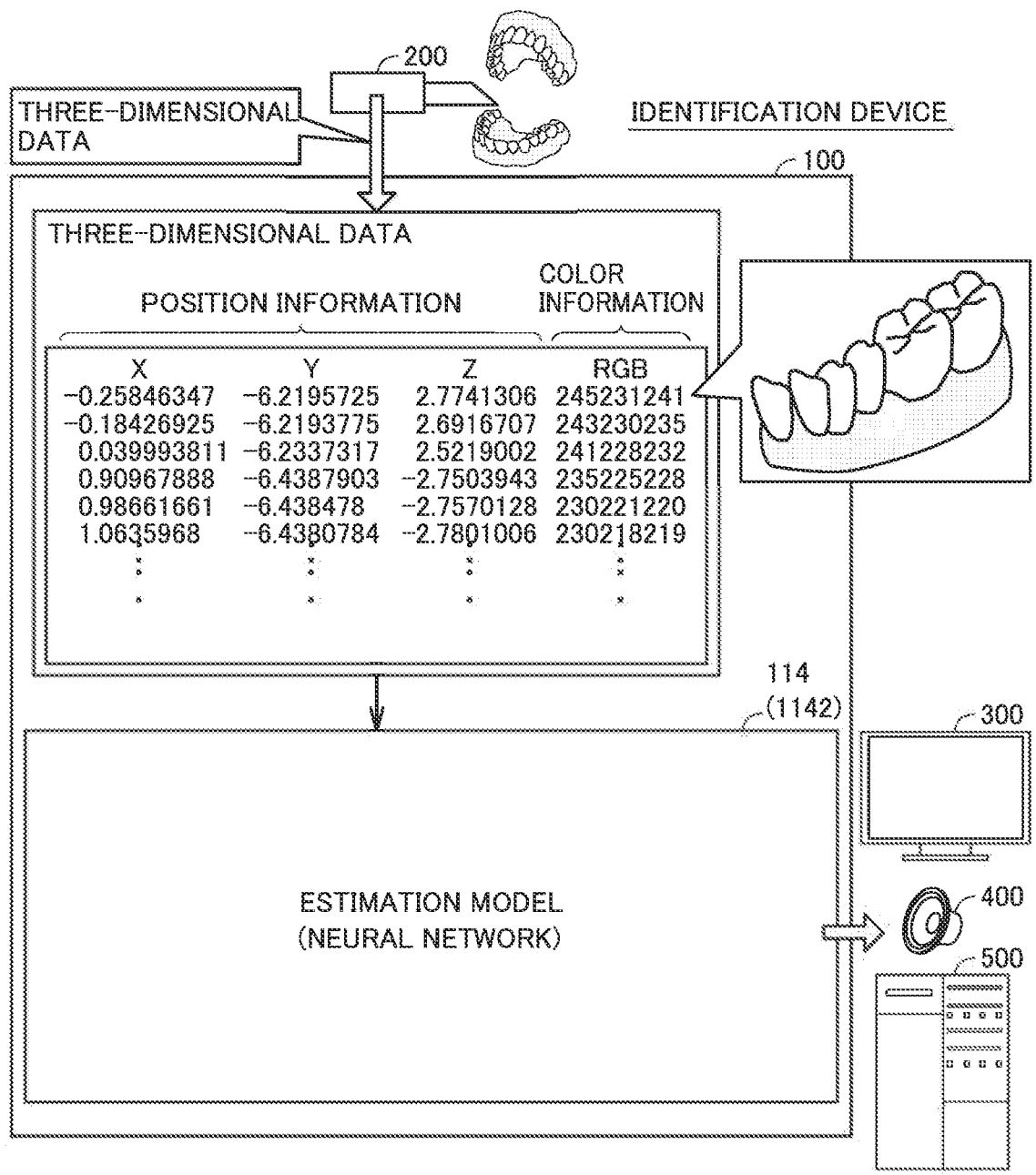
FIG. 6 is a schematic diagram for illustrating an identification process by the identification device according to the present embodiment.

An example of the identification process by identification device 100 according to the present embodiment will be hereinafter described with reference to FIGS. 5 to 7. FIG. 5 is a schematic diagram showing a functional configuration of identification device 100 according to the present embodiment. FIG. 6 is a schematic diagram for illustrating the identification process by identification device 100 according to the present embodiment. FIG. 7 is a schematic diagram showing examples of teeth to be identified in the identification process according to the present embodiment. In FIG. 7, teeth to be scanned by three-dimensional scanner 200 are represented by diagrammatic drawings.

As shown in FIG. 5, identification device 100 includes an input unit 1102, a profile acquisition unit 1119, an identification unit 1130, and an output unit 1103, each of which is provided as a functional unit related to the identification process. Each of these functions is implemented by computing device 130 of identification device 100 executing an OS 127 and identification program 120.

Input unit 1102 receives three-dimensional data acquired by three-dimensional scanner 200. Profile acquisition unit 1119 acquires profile data 119 of subject 2. Based on the three-dimensional data input into input unit 1102 and profile data 119 of subject 2 acquired by profile acquisition unit 1119, identification unit 1130 performs an identification process of identifying a type of a tooth using estimation model 114 (learned model 114a).

Estimation model 114 includes a neural network 1142 and a parameter 1144 used by neural network 1142. Parameter 1144 includes a weighting factor used for calculation by neural network 1142 and a determination value used for determination of identification. Output unit 1103 outputs the identification result obtained by identification unit 1130 to display 300, speaker 400, and server device 500.

In this case, as shown in FIG. 6, the three-dimensional data input into input unit 1102 includes three-dimensional position information at each of points of a tooth and color information at each of points of a tooth. In the identification process, the position information is used. The position information includes coordinates of an absolute position in three dimensions with respect to a predetermined position. For example, the position information includes coordinates of an absolute position on each of axes including an X axis (for example, an axis of a tooth in the horizontal direction), a Y axis (for example, an axis of a tooth in the vertical direction), and a Z axis (for example, an axis of a tooth in the height direction) with reference to a central position at each of points of a tooth as an origin point. The position information is not limited to the coordinates of an absolute position in three dimensions with respect to a predetermined position, but may include coordinates of a relative position in three dimensions indicating the distance from an adjacent point, for example.

In this case, as shown in FIG. 7, when the tooth to be scanned by three-dimensional scanner 200 is an incisor in an upper jaw, user 1 scans the inside of the oral cavity of subject 2 such that the three-dimensional image to be obtained includes at least: an image of an area on the upper lip side; an image of an area on the palate side; and an image of an area on the incisal edge side. When the teeth to be scanned by three-dimensional scanner 200 are a canine and a molar in the upper jaw, user 1 scans the inside of the oral cavity of subject 2 such that the three-dimensional image to be obtained includes at least: an image of an area on the buccal side; an image of an area on the palate side; and an image of an occlusion area. When the tooth to be scanned by three-dimensional scanner 200 is an incisor in the lower jaw, user 1 scans the inside of the oral cavity of subject 2 such that the three-dimensional image to be obtained includes at least: an image of an area on the lower lip side; an image of an area on the tongue side; and an image of an area on the incisal edge side. When the teeth to be scanned by three-dimensional scanner 200 are a canine and a molar in the lower jaw, user 1 scans the inside of the oral cavity of subject 2 such that the three-dimensional image to be obtained includes at least: an image of an area on the buccal side; an image of an area on the tongue side; and an image of an occlusion area.

In general, the teeth of subject 2 vary in shape and size depending on their types. For example, in the case of an incisor in the upper jaw, the plane on the upper lip side generally has a U-shape. In the case of a canine in the upper jaw, the plane on the buccal side generally has a pentagonal shape. Each tooth has a characteristic shape and a characteristic size depending on its type. Based on the three-dimensional data obtained by digitizing such a characteristic shape and a characteristic size, identification unit 1130 uses estimation model 114 to identify a type of a tooth corresponding to the three-dimensional data.

As shown in FIG. 6, estimation model 114 includes neural network 1142. In neural network 1142, a value of the position information included in the three-dimensional data input into input unit 1102 is input to an input layer. Then, in neural network 1142, for example, by the intermediate layer, the input value of the position information is multiplied by a weighting factor, and a predetermined bias is added to the input value of the position information, and also, calculation with a predetermined function is performed. Then, the calculation result is compared with the determination value. Further, in neural network 1142, the result obtained by the above-mentioned calculation and determination is output as the identification result from the output layer. The calculation and determination by neural network 1142 may be performed by any method as long as a tooth can be identified based on the three-dimensional data.

In neural network 1142 of estimation model 114, the intermediate layer has a multi-layered structure, and thus, a process by deep learning is performed. In the present embodiment, examples of identification program 120 for performing an identification process specialized for a three-dimensional image may be VoxNet, 3D ShapeNets, Multi-View CNN, RotationNet, OctNet, FusionNet, PointNet, PointNet++, SSCNet, MarrNet, and the like, but other programs may be used. An existing mechanism may also be applied to neural network 1142.

In such a configuration, when identification device 100 receives three-dimensional data corresponding to a three-dimensional image including a plurality of teeth, identification device 100 can extract respective features of the teeth using neural network 1142 of estimation model 114 based on the three-dimensional data, and then identify respective types of the teeth based on the extracted features of the teeth. Further, as shown in FIG. 6, identification device 100 receives not only a target tooth to be identified but also three-dimensional data including data of teeth adjacent to this target tooth, and thereby, neural network 1142 of estimation model 114 can extract the feature of the target tooth also in consideration of the relation with the shapes of the adjacent teeth. Identification device 100 can extract not only a tooth feature that is generally recognized but also a tooth feature that is not generally recognized, and thereby, can accurately identify a type of a tooth.

The neural network included in estimation model 514 held in server device 500 has the same configuration as that of neural network 1142 included in estimation model 114 shown in FIG. 6.

[Generation of Learning Data]

Figure 8:
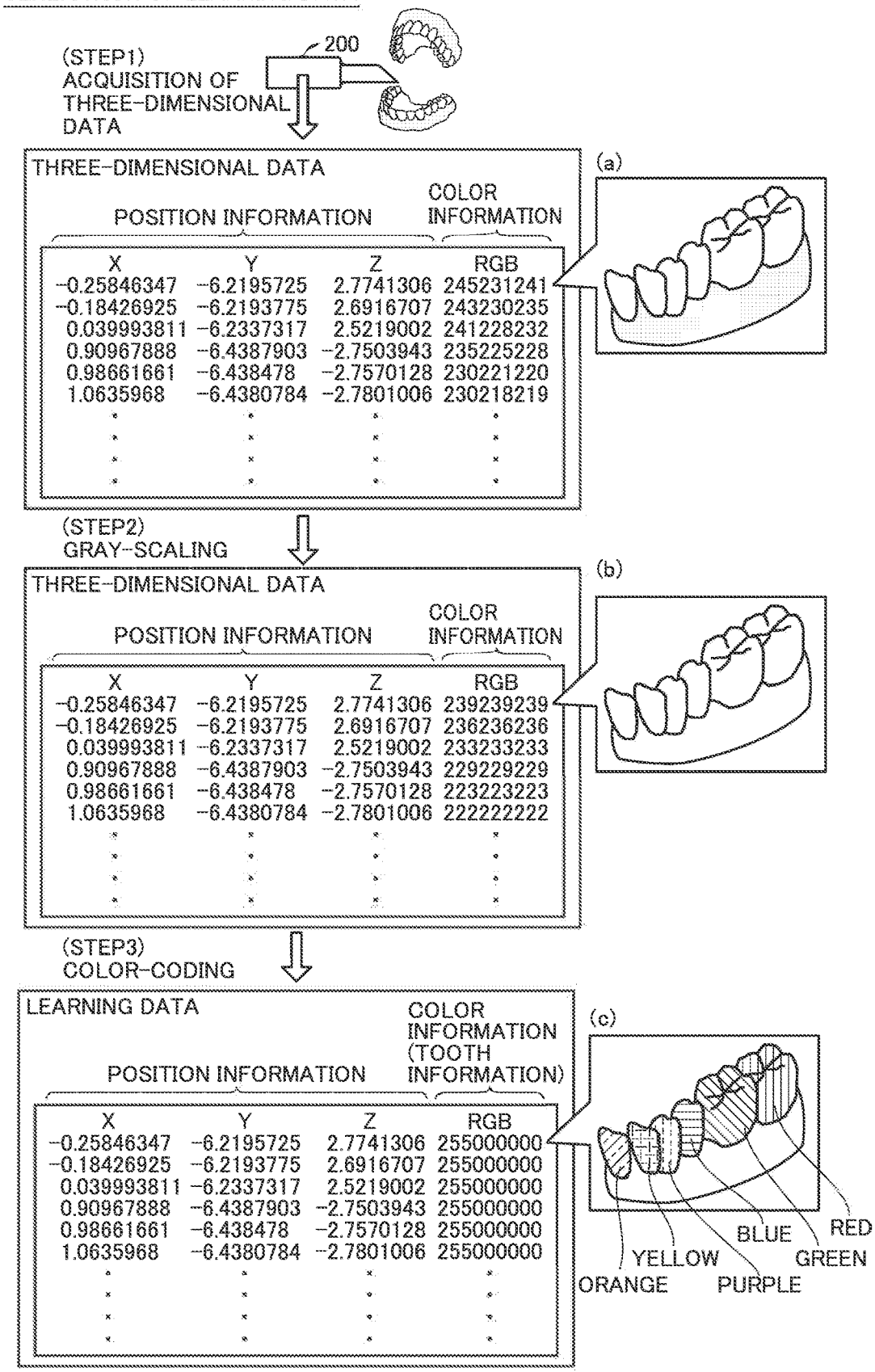
FIG. 8 is a schematic diagram for illustrating generation of learning data according to the present embodiment.
Figure 9:
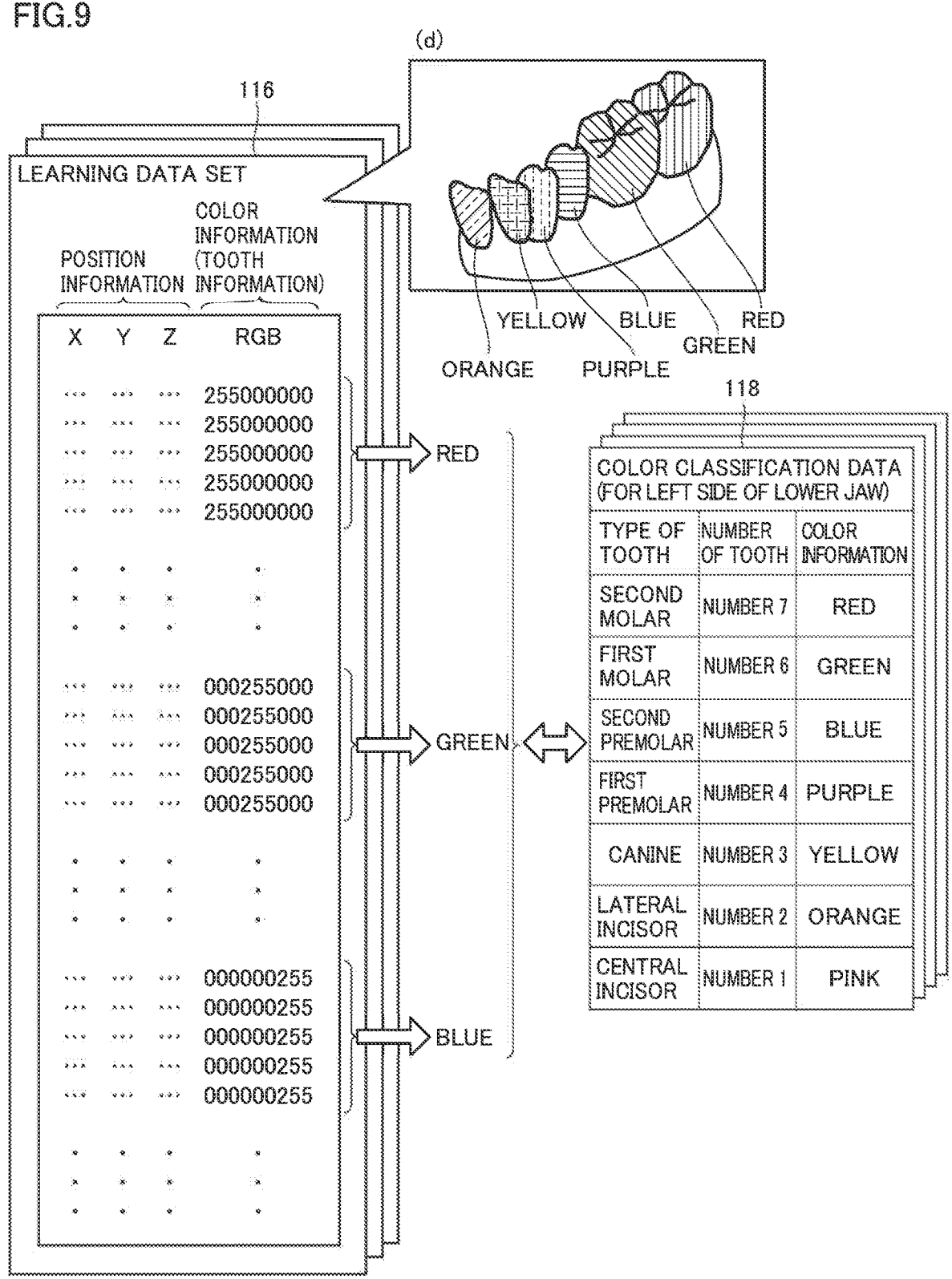
FIG. 9 is a schematic diagram for illustrating an example of a learning data set according to the present embodiment.

An example of generation of learning data set 116 will be hereinafter described with reference to FIGS. 8 and 9. FIG. 8 is a schematic diagram for illustrating generation of the learning data according to the present embodiment. FIG. 9 is a schematic diagram for illustrating an example of learning data set 116 according to the present embodiment.

As shown in FIG. 8, three-dimensional data is first acquired by three-dimensional scanner 200 (STEP 1). The three-dimensional data acquired by three-dimensional scanner 200 includes three-dimensional position information at each of points of a tooth corresponding to the three-dimensional data and color information (RGB values) at each of points of the tooth. When a three-dimensional image is generated based on the three-dimensional data acquired by three-dimensional scanner 200, a three-dimensional image including teeth in actual colors is generated as shown in FIG. 8(a).

Then, a noise removing process is performed as a preparation for a color-coding process for each tooth, which will be described later. For example, in the present embodiment, a three-dimensional image corresponding to the three-dimensional data is gray-scaled (STEP 2). The three-dimensional image is gray-scaled by user 1 (in this case, an engineer of a manufacturer, an operator in a manufacturing factory or the like who generates learning data). When the three-dimensional image is gray-scaled, a three-dimensional image including gray-scaled teeth is generated as shown in FIG. 8(b). Further, as the three-dimensional image is gray-scaled, the color information (RGB values) at each of points of a tooth corresponding to the three-dimensional data is changed to a value corresponding to the gray scale level.

Then, predetermined colors are applied to the respective teeth included in the three-dimensional image corresponding to the three-dimensional data, and thereby, the teeth are color-coded (STEP 3). For example, as shown in FIG. 9, color classification data 118 held in identification device 100 is provided for each of areas inside the oral cavity, such as the left side in the lower jaw, the right side in the lower jaw, the left side in the upper jaw, and the right side in the upper jaw. FIG. 9 shows color classification data 118 corresponding to the left side in the lower jaw. In each color classification data 118, tooth numbers generally used in the dental field and predetermined color information are assigned for each type of tooth.

For example, the second molar is assigned number 7 as a tooth number and assigned red as color information. The first molar is assigned number 6 as a tooth number and assigned green as color information. The second premolar is assigned number 5 as a tooth number and assigned blue as color information. In this way, in each color classification data 118, the tooth number and the color information are assigned in advance for each type of tooth.

Application of colors to the respective teeth is performed by user 1 (such as an engineer of a manufacturer or an operator in a manufacturing factory). Specifically, user 1 identifies a type of each tooth included in the three-dimensional image based on his/her knowledge, specifies colors corresponding to the identified types of teeth while referring to color classification data 118, and then, applies the specified colors to the images of the respective teeth.

For example, when user 1 identifies the tooth included in the three-dimensional image as the second molar, user 1 applies a red color to an image of the tooth. When user 1 identifies the tooth included in the three-dimensional image as the first molar, user 1 applies a green color to an image of the tooth. Application of predetermined colors to the respective teeth included in the three-dimensional image results in generation of a three-dimensional image including teeth to which their respective predetermined colors are applied as shown in FIGS. 8(c) and 9(d). For easy recognition, each color is shown by hatching in these figures.

Further, in accordance with the color-coding of the teeth, the color information (RGB values) at each point of each of the teeth corresponding to the three-dimensional data is changed to a value corresponding to the color applied to each tooth. For example, the color information (RGB values) is "255000000" for each position coordinate of the second molar in red color; the color information (RGB values) is "000255000" for each position coordinate of the first molar in green color; and the color information (RGB values) is "00000255" for each position coordinate of the second premolar in blue color. In other words, predetermined color information (RGB values) is associated with each of points of a tooth corresponding to the three-dimensional data.

When the predetermined color information is associated with each tooth, the three-dimensional data includes position information and color information that corresponds to the applied color. Then, such three-dimensional data is employed as learning data. In other words, in the learning data according to the present embodiment, the color information corresponding to each type of tooth is associated (labeled) with the position information referred to in the identification process. Further, the color information is associated with the three-dimensional data such that the range of each of the teeth corresponding to the three-dimensional data can be specified. Specifically, the same color information is associated for each position information corresponding to each tooth. A collection of such learning data is held in identification device 100 as learning data set 116.

Thus, when generating learning data, user 1 applies colors to the respective teeth included in the three-dimensional image to thereby label the correct data, which provides many advantages. For example, in the case of labeling with simple characters or symbols, it is difficult for user 1 to recognize the range of each tooth. However, in the case of labeling by color-coding, application of colors allows user 1 to readily recognize the boundary between a target tooth to be labeled and a tooth adjacent to the target tooth, and the boundary between a target tooth to be labeled and gums. Further, user 1 applies colors while checking the three-dimensional image from various angles during labeling. Even when the angle at which the image is viewed is changed, user 1 still readily recognizes a specific range in which application of colors to the teeth that are being labeled has completed.

In the present embodiment, based on the knowledge of user 1, user 1 manually applies colors to the respective teeth included in the three-dimensional image. However, such a manual operation can also be partially performed complementarily by software. For example, the boundary between a target tooth to be labeled and a tooth adjacent to the target tooth and the boundary between a target tooth to be labeled and gums may be specified by edge detection, which allows extraction of only the target tooth to be labeled.

Further, generation of learning data set 116 shown in FIGS. 8 and 9 is also applicable to generation of learning data set 516 held in server device 500. For example, learning data set 116 shown in FIG. 9 may be applied to learning data set 516 held in server device 500, or color classification data 118 shown in FIG. 9 may be applied to color classification data 518 held in server device 500.

[Generation of Learned Model]

Figure 10:
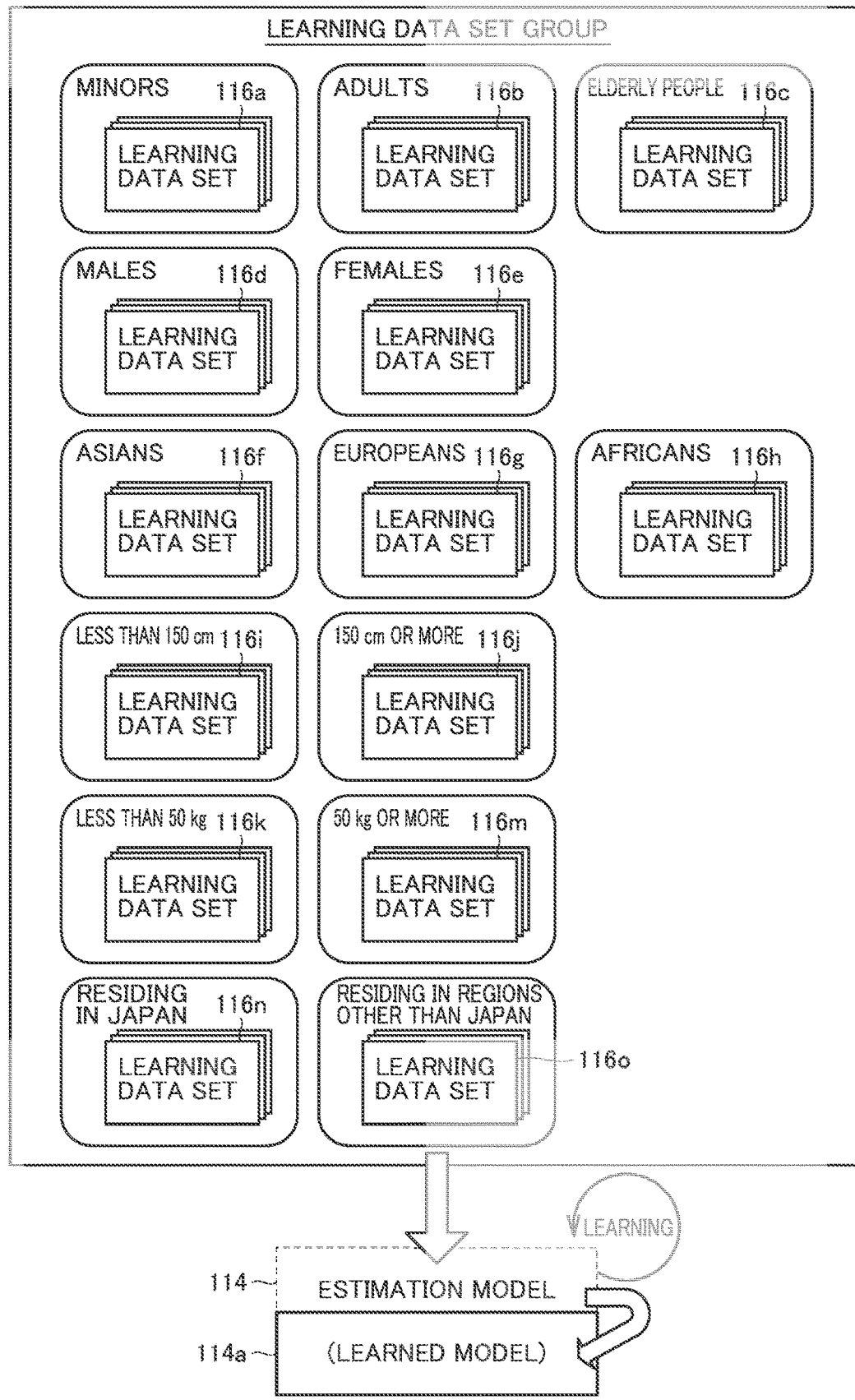
FIG. 10 is a schematic diagram for illustrating generation of a learned model based on the learning data set according to the present embodiment.

An example of generation of learned model 114a will be hereinafter described with reference to FIG. 10. FIG. 10 is a schematic diagram for illustrating generation of learned model 114a based on learning data set 116 according to the present embodiment.

As shown in FIG. 10, learning data set 116 can be classified for each category based on the profile of subject 2 as a target to be scanned when learning data set 116 is generated. For example, the learning data sets generated from the three-dimensional data including data of teeth of applicable subject 2 can be assigned to an age (minors, adults, elderly people), a gender (males, females), a race (Asians, Europeans, Africans), a height (less than 150 cm, 150 cm or more), a weight (less than 50 kg, 50 kg or more), and a place of residence (residing in Japan, residing in regions other than Japan). The layers of the respective categories can be set as appropriate. For example, ages can be stratified in greater detail for each prescribed age difference (in this case, for each 3 years of age), specifically for age 0 to age 3, age 4 to age 6, age 7 to age 9, and the like.

Identification device 100 generates learned model 114a by learning estimation model 114 using a plurality of learning data sets 116a to 116o that can be classified for each category. There may be an overlap among the pieces of learning data depending on how the categories are classified. In the case where there is an overlap among the pieces of learning data, only one piece of learning data has to be used for learning of estimation model 114.

In general, a tooth shape varies in feature depending on genetics or living environments such as an age, a gender, a race, a height, a weight, and a place of residence. For example, in general, permanent teeth of an adult are larger than primary teeth of a child, and also, permanent teeth are different in shape from primary teeth. In general, male teeth are larger than female teeth, and also, male teeth are different in shape from female teeth. In general, European teeth tend to be pointed at their tips so as to allow the Europeans to easily bite off hard meat and bread, whereas Japanese teeth tend to be smooth at their tips so as to allow the Japanese to easily mash soft rice and vegetables. Accordingly, the learning process is performed based on the profile data as in the present embodiment, to thereby allow generation of a learned model that allows identification of a type of a tooth in consideration of genetics, living environments or the like.

It should be noted that generation of learned model 114a shown in FIG. 10 is also applicable to generation of learned model 514a held in server device 500. For example, learning data sets 116a to 116o shown in FIG. 10 may be applied to learning data set 516 held in server device 500, or estimation model 114 shown in FIG. 10 may be applied to estimation model 514 held in server device 500.

[Learning Process of Identification Device]

Figure 11:
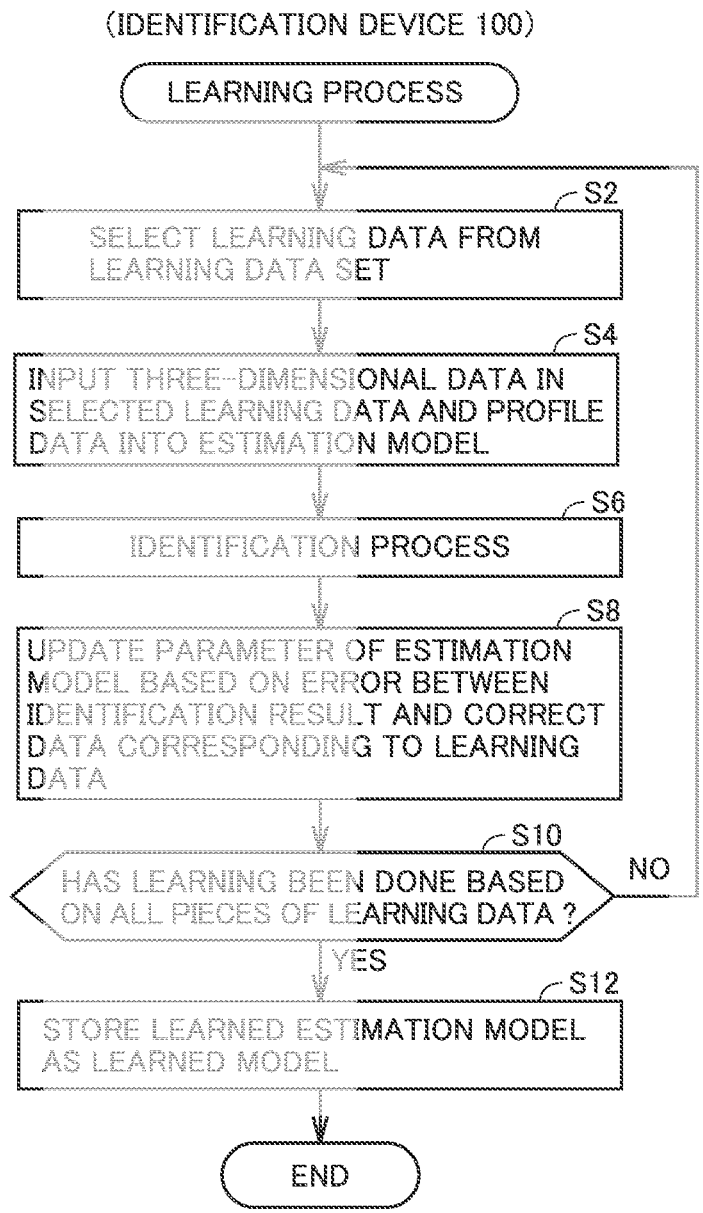
FIG. 11 is a flowchart for illustrating an example of a learning process performed by the identification device according to the present embodiment.

The learning process performed by identification device 100 will be hereinafter described with reference to FIG. 11. FIG. 11 is a flowchart for illustrating an example of the learning process performed by identification device 100 according to the present embodiment. Each of steps shown in FIG. 11 is implemented by computing device 130 of identification device 100 executing OS 127 and learning program 121.

As shown in FIG. 11, from learning data set 116, identification device 100 selects learning data to be used for learning (S2). Specifically, identification device 100 selects one piece or a plurality of pieces of learning data from learning data set 116 included in a learning data set group shown in FIG. 10. Identification device 100 does not necessarily have to automatically select learning data, but may use the learning data selected by user 1 for the learning process.

Identification device 100 inputs, into estimation model 114, the position information of the three-dimensional data included in the selected learning data and the profile data of subject 2 as a target to be scanned during generation of the learning data (S4). At this time, the correct data labeled in the three-dimensional data is not input into identification device 100. Based on the feature of a tooth corresponding to the three-dimensional data, identification device 100 performs an identification process of identifying a type of the tooth using estimation model 114 (S6). In the identification process, identification device 100 identifies a type of the tooth using estimation model 114 based on the profile data in addition to the three-dimensional data.

Identification device 100 updates parameter 1144 of estimation model 114 based on the error between the identification result about the type of the tooth identified by the identification process and the correct data corresponding to the learning data used in the learning process (S8).

For example, as a result of the identification based on the position information of a specific tooth, identification device 100 estimates color information corresponding to this specific tooth. Identification device 100 compares the color information (correct data) corresponding to the specific tooth included in the learning data with the color information estimated by identification device 100 itself. Then, when these pieces of color information match with each other, identification device 100 maintains parameter 1144 of estimation model 114. In contrast, when these pieces of color information do not match with each other, identification device 100 updates parameter 1144 of estimation model 114 such that these pieces of color information match with each other.

Alternatively, as a result of the identification made on the position information of a specific tooth, identification device 100 estimates color information corresponding to this specific tooth, and specifies the type of the tooth and the number of the tooth (the correct data) that correspond to the color information based on color classification data 118. Identification device 100 compares the type of the tooth and the number of the tooth (the correct data) that are assigned to the color information corresponding to the specific tooth included in the learning data with the type of the tooth and the number of the tooth that are estimated by identification device 100 itself. Then, when the types match with each other and the numbers match with each other, identification device 100 maintains parameter 1144 of estimation model 114. When the types do not match with each other and the numbers do not match with each other, identification device 100 updates parameter 1144 of estimation model 114 such that the types match with each other and the numbers match with each other.

Then, identification device 100 determines whether learning has been done based on all the pieces of learning data (S10). When learning has not been done based on all the pieces of learning data (NO in S10), identification device 100 returns to the process in S2.

On the other hand, when learning has been done based on all the pieces of learning data (YES in S10), identification device 100 stores learned estimation model 114 as learned model 114a (S12), and then ends the present process.

In this way, identification device 100 can generate learned model 114a by learning estimation model 114 based on the identification result about the type of the tooth that is obtained using the three-dimensional data obtained by the identification process, assuming that the tooth information (the color information, the tooth name, the tooth number, or the like) corresponding to the type of the tooth associated with the three-dimensional data included in the learning data is defined as correct data.

Further, in the learning process, identification device 100 learns estimation model 114 in consideration of the profile data in addition to the learning data, so that it can generate learned model 114a in consideration of the profile of subject 2.

[Learning Process of Server Device]

Figure 12:
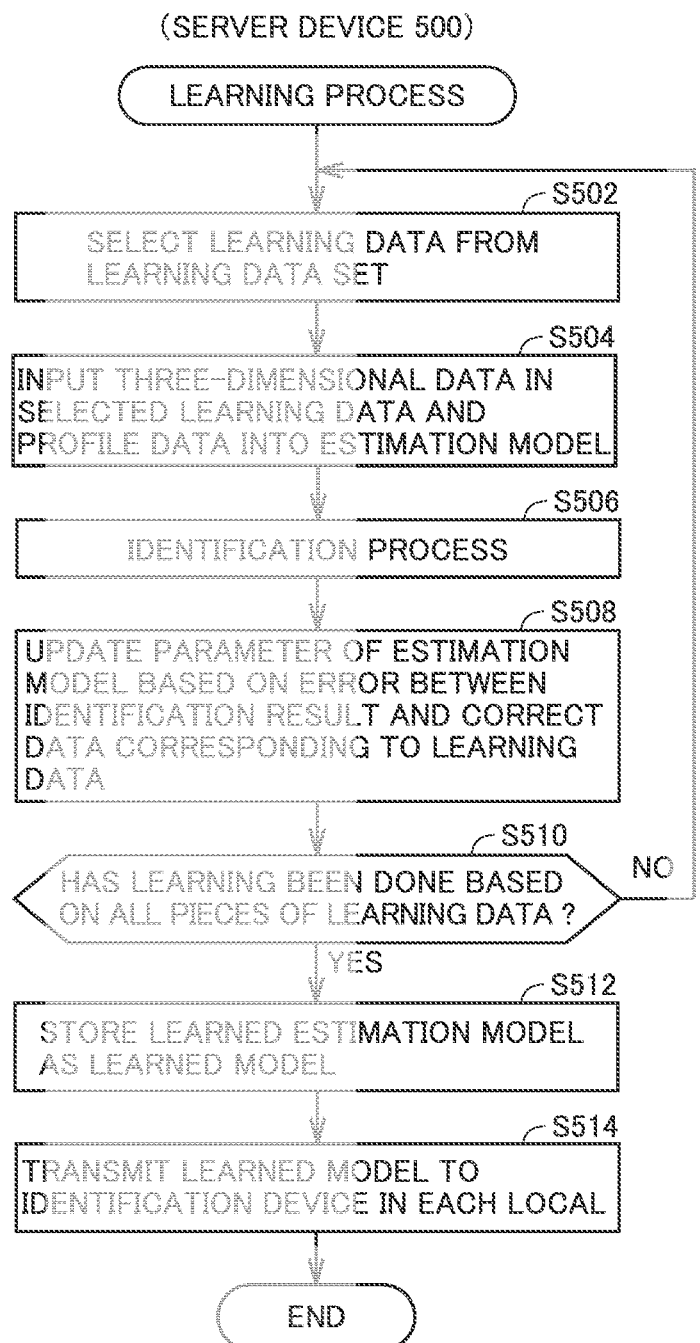
FIG. 12 is a flowchart for illustrating an example of a learning process performed by the server device according to the present embodiment.

The learning process performed by server device 500 will be hereinafter described with reference to FIG. 12. FIG. 12 is a flowchart for illustrating an example of the learning process performed by server device 500 according to the present embodiment. Each of steps shown in FIG. 12 is implemented by computing device 530 of server device 500 executing OS 527 and learning program 521.

As shown in FIG. 12, from the learning data set, server device 500 selects learning data to be used for learning (S502). In this case, the learning data may be generated using the big data accumulated by server device 500 and stored therein. For example, server device 500 may generate, in advance, learning data using three-dimensional data included in the scan information acquired from identification device 100 in each of locals A to C and the dental laboratory, and then, perform the learning process using the generated learning data. Server device 500 does not necessarily have to automatically select the learning data, but may use the learning data selected by user 1 for the learning process.

Server device 500 inputs, into estimation model 514, the three-dimensional data (the position information) included in the selected learning data and the profile data of subject 2 as a target to be scanned during generation of the learning data (S504). At this time, the correct data labeled in the three-dimensional data is not input into server device 500. Based on the feature of a tooth corresponding to the three-dimensional data, server device 500 performs the identification process of identifying a type of this tooth by using estimation model 514 (S506). In the identification process, based on the profile data in addition to the three-dimensional data, server device 500 identifies a type of the tooth using estimation model 514.

Then, server device 500 updates the parameter of estimation model 514 based on the error between the identification result about the type of the tooth identified by the identification process and the correct data corresponding to the learning data used for learning (S508).

For example, as a result of the identification based on the position information about a specific tooth, server device 500 estimates the color information corresponding to the specific tooth. Server device 500 compares the color information (the correct data) corresponding to the specific tooth included in the learning data set with the color information estimated by server device 500 itself. Then, when these pieces of color information match with each other, server device 500 maintains the parameter of estimation model 514. In contrast, when these pieces of color information do not match with each other, server device 500 updates the parameter of estimation model 514 such that these pieces of color information match with each other.

Alternatively, as a result of the identification based on the position information of a specific tooth, server device 500 estimates the color information corresponding to the specific tooth, and then specifies a type of the tooth and the number of the tooth (correct data) that correspond to the color information based on color classification data 518. Then, server device 500 compares the type of the tooth and the number of the tooth (correct data) that are assigned to the color information corresponding to the specific tooth included in the learning data set with the type of the tooth and the number of the tooth that are estimated by server device 500 itself. When the types match with each other and the numbers match with each other, server device 500 maintains the parameter of estimation model 514. In contrast, when the types do not match with each other and the numbers do not match with each other, server device 500 updates the parameter of estimation model 514 such that the types match with each other and the numbers match with each other.

Then, server device 500 determines whether learning has been done or not based on all the pieces of learning data (S510). When learning has not been done based on all the pieces of learning data (NO in S510), server device 500 returns to the process in S502.

On the other hand, when learning has been done based on all the pieces of learning data (YES in S510), server device 500 stores learned estimation model 514 as learned model 514a (S512). Then, server device 500 transmits the generated learned model 514a to identification device 100 in each local (S514), and then, ends the process.

In this way, server device 500 can generate learned model 514a by learning estimation model 514 based on the identification result about the type of the tooth that is obtained using the three-dimensional data obtained by the identification process, assuming that the tooth information (the color information, the tooth name, the tooth number, or the like) corresponding to the type of the tooth associated with the three-dimensional data included in the learning data is defined as correct data.

Further, in the learning process, server device 500 learns estimation model 514 in consideration of the profile data in addition to the learning data, so that it can generate learned model 514a in consideration of the profile of subject 2.

Further, server device 500 uses the three-dimensional data included in the scan information acquired from identification device 100 in each of locals A to C and the dental laboratory as the learning data used in the learning process. Thus, server device 500 can perform the learning process based on more learning data than that in the learning process performed for each identification device 100, and also, can generate learned model 514a that allows identification of a type of a tooth with higher accuracy.

[Service Providing Process of Identification Device]

Figure 13:
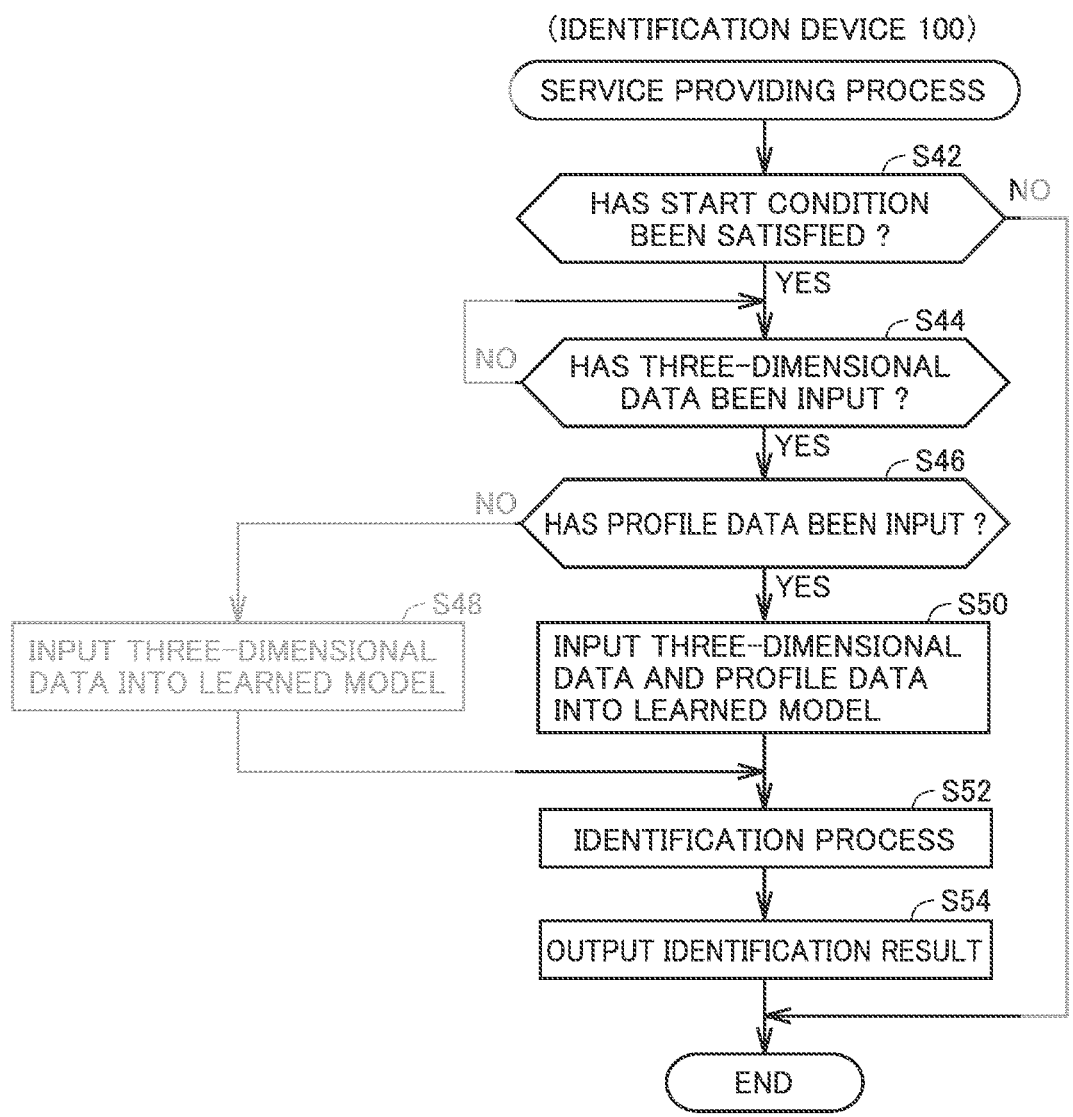
FIG. 13 is a flowchart for illustrating an example of a service providing process performed by the identification device according to the present embodiment.

The service providing process performed by identification device 100 will be hereinafter described with reference to FIG. 13. FIG. 13 is a flowchart for illustrating an example of the service providing process performed by identification device 100 according to the present embodiment. Each of steps shown in FIG. 13 is implemented by computing device 130 of identification device 100 executing OS 127 and identification program 120.

As shown in FIG. 13, identification device 100 determines whether a start condition for the service providing process has been satisfied or not (S42). The start condition may be satisfied, for example, when the power supply of three-dimensional scanner 200 is started, or upon switching to a mode corresponding to the service providing process after the power supply of three-dimensional scanner 200 is started. Alternatively, the start condition may be satisfied when a start switch is operated after an icon corresponding to the service providing process (for example, an AI assist icon) is operated and turned into a blinking state. The start condition may be satisfied when a prescribed amount of three-dimensional data is acquired. The start condition may be any condition as long as it is satisfied when any action is performed on three-dimensional scanner 200.

When the start condition has not been satisfied (NO in S42), identification device 100 ends the process. On the other hand, when the start condition has been satisfied (YES in S42), identification device 100 determines whether the three-dimensional data has been input or not (S44). For example, identification device 100 determines whether a sufficient amount of three-dimensional data for performing the identification process has been input or not. When a sufficient amount of three-dimensional data has not been input (NO in S44), identification device 100 repeats the process in S44.

On the other hand, when a sufficient amount of three-dimensional data has been input (YES in S44), identification device 100 determines whether the profile data of subject 2 has been input or not by user 1 (S46). When the profile data has not been input (NO in S46), identification device 100 inputs the three-dimensional data (the position information) into learned model 114a (S48). On the other hand, when the profile data has been input (YES in S46), identification device 100 inputs the three-dimensional data (the position information) and the profile data into learned model 114a (S50). The learned model used in this case is not limited to learned model 114a generated by identification device 100 in the learning process shown in FIG. 11, but may be learned model 514a generated by server device 500 in the learning process shown in FIG. 12.

After S48 and S50, based on the feature of a tooth corresponding to the three-dimensional data, identification device 100 performs an identification process of identifying a type of this tooth using learned model 114a (S52). In this case, when the profile data has been input into learned model 114a in S50, identification device 100 identifies a type of the tooth using learned model 114a based on the profile data in addition to the three-dimensional data. In this case, the type of the tooth can be identified more accurately than in the case where the type of the tooth is identified using learned model 114a based only on the three-dimensional data.

Then, identification device 100 outputs the identification result obtained by the identification process to display 300, speaker 400, server device 500, and the like (S54), and then, ends the present process.

In this way, based on the feature of the tooth corresponding to the input three-dimensional data, identification device 100 identifies a type of this tooth using learned model 114a. Thus, identification device 100 can identify a type of a tooth more accurately than in the case where a type of a tooth is identified depending on the user's knowledge.

Further, in the identification process, identification device 100 identifies a type of a tooth in consideration of the profile data in addition to the input three-dimensional data, thereby allowing more accurate identification of a type of a tooth.

[Main Configuration]

As described above, the present embodiment includes the following disclosure.

An identification device 100 includes: an input unit 1102 that receives three-dimensional data including data of the tooth; an identification unit 1130 that identifies a type of the tooth based on the three-dimensional data including a feature of the tooth received by input unit 1102 and an estimation model 114 (a learned model 114a) including a neural network 1142; and an output unit 1103 that outputs an identification result obtained by identification unit 1130. Estimation model 114 is learned based on tooth information corresponding to a type of the tooth associated with the three-dimensional data and the identification result including the type of the tooth that is obtained using the three-dimensional data.

Accordingly, user 1 inputs the three-dimensional data including data of a tooth into estimation model 114 (learned model 114a) including neural network 1142, and thus can identify a type of the tooth, thereby allowing more accurate identification of a type of a tooth than in the case where a type of a tooth is identified depending on the user's knowledge.

The learning of estimation model 114 may be implemented by learning of estimation model 514 executed by server device 500.

Input unit 1102 receives at least the three-dimensional data corresponding to a plurality of teeth adjacent to the tooth and gums in an oral cavity, and identification unit 1130 identifies a type of each of the teeth based on the three-dimensional data including a feature of each of the teeth.

Accordingly, user 1 inputs the three-dimensional data corresponding to a plurality of teeth adjacent to each other and gums in an oral cavity into estimation model 114 (learned model 114a) including neural network 1142, and thereby, can identify a type of each of the teeth. Thus, a type of a tooth can be identified more accurately and smoothly than in the case where types of teeth are identified one by one depending on the user's knowledge. Further, user 1 can extract a feature of a tooth by estimation model 114 including neural network 1142 also in consideration of the relation with the shapes of the adjacent teeth, thereby allowing accurate identification of a type of a tooth.

As shown in FIG. 6, the three-dimensional data includes three-dimensional position information at each of a plurality of points forming the tooth corresponding to the three-dimensional data.

Accordingly, user 1 inputs the three-dimensional position information at each of a plurality of points forming a tooth corresponding to the three-dimensional data into estimation model 114 (learned model 114a) including neural network 1142, and thereby, can identify a type of the tooth.

As shown in FIG. 6, the position information includes coordinates of an absolute position based on a predetermined position.

Accordingly, user 1 inputs coordinates of an absolute position based on a predetermined position as the three-dimensional position information at each of points of a tooth corresponding to the three-dimensional data into estimation model 114 (learned model 114a) including neural network 1142, and thereby, can identify a type of the tooth.

As shown in FIG. 7, in a case where the tooth corresponding to the three-dimensional data received by input unit 1102 is an incisor in an upper jaw, a three-dimensional image corresponding to the three-dimensional data includes at least: an image of an area on an upper lip side; an image of an area on a palate side; and an image of an area on an incisal edge side. Also, in a case where the tooth corresponding to the three-dimensional data received by input unit 1102 is each of a canine and a molar in the upper jaw, the three-dimensional image corresponding to the three-dimensional data includes at least: an image of an area on a buccal side, an image of an area on a palate side, and an image of an occlusion area. Also, in a case where the tooth corresponding to the three-dimensional data received by input unit 1102 is an incisor in a lower jaw, the three-dimensional image corresponding to the three-dimensional data includes at least: an image of an area on a lower lip side; an image of an area on a tongue side; and an image of an area on an incisal edge side. Also, in a case where the tooth corresponding to the three-dimensional data received by input unit 1102 is each of a canine and a molar in the lower jaw, the three-dimensional image corresponding to the three-dimensional data includes at least: an image of an area on a buccal side, an image of an area on a tongue side, and an image of an occlusion area.

Accordingly, user 1 can identify a type of a tooth using estimation model 114 (learned model 114a) including neural network 1142 for each of an incisor in the upper jaw, a canine and a molar in the upper jaw, an incisor in the lower jaw, and a canine and a molar in the lower jaw.

As shown in FIGS. 1 and 5, output unit 1103 outputs the identification result to display 300. Display 300 shows at least one of an image, a character, a numeral, an icon, and a symbol that correspond to the identification result.

Accordingly, display 300 shows an image corresponding to the identification result obtained through estimation model 114 (learned model 114a) including neural network 1142. Thus, user 1 can intuitively recognize the identification result, thereby improving the convenience.

As shown in FIGS. 1 and 5, output unit 1103 outputs the identification result to speaker 400. Then, speaker 400 outputs a sound corresponding to the identification result.

Accordingly, speaker 400 outputs a sound corresponding to the identification result obtained through estimation model 114 (learned model 114a) including neural network 1142. Thus, user 1 can intuitively recognize the identification result, thereby improving the convenience.

As shown in FIGS. 1 and 5, output unit 1103 outputs the identification result to server device 500. Then, server device 500 stores an accumulation of the identification result.

Accordingly, server device 500 stores an accumulation of the identification result to thereby form big data. Thus, for example, user 1 causes server device 500 to perform the learning process using such big data, and thereby can generate a learned model that allows more accurate identification of a type of a tooth.

As shown in FIG. 5, estimation model 114 includes at least one of a weighting factor and a determination value as parameter 1144 used by neural network 1142. Also, estimation model 114 is learned by updating parameter 1144 based on the tooth information and the identification result.

Accordingly, user 1 updates parameter 1144 of estimation model 114, and thereby can generate learned model 114a that allows more accurate identification of a type of a tooth.

As shown in FIG. 9, the tooth information includes at least one piece of information of a color, a character, a numeral, and a symbol that are associated with a type of the tooth corresponding to the three-dimensional data.

Accordingly, user 1 can generate learned model 114a that allows more accurate identification of a type of a tooth based on the color, the character, the numeral, the symbol, and the like that are associated with the type of the tooth.

As shown in FIG. 9, the tooth information is associated with the three-dimensional data to allow a range of each of a plurality of the teeth corresponding to the three-dimensional data to be specified.

Accordingly, user 1 can specify a range of each of the plurality of teeth based on the tooth information, thereby improving the convenience during labeling.

As shown in FIG. 9, the tooth information is associated with each of a plurality of points forming the tooth corresponding to the three-dimensional data.

Accordingly, since the tooth information is associated with each of a plurality of points forming a tooth corresponding to the three-dimensional data, user 1 can finely associate the tooth information with each tooth, thereby improving the convenience during labeling.

The estimation model is learned based on attribute information related to a subject 2 having the teeth, in addition to the tooth information and the identification result.

Accordingly, user 1 can implement learning of estimation model 114 based on the attribute information related to subject 2 in addition to the learning data, thereby allowing generation of a learned model in consideration of the attribute information about subject 2.

As shown in FIG. 10, the attribute information includes at least one piece of information of an age, a gender, a race, a height, a weight, and a place of residence about the subject.

Accordingly, user 1 can implement learning of estimation model 114 based on at least one of an age, a gender, a race, a height, a weight, and a place of residence about the subject in addition to the learning data, thereby allowing generation of learned model 114*a* in consideration of the profile of subject 2.

A scanner system 10 includes: a three-dimensional scanner 200 that acquires three-dimensional data including data of the tooth using a three-dimensional camera; and an identification device 100 that identifies a type of the tooth based on the three-dimensional data including a feature of the tooth acquired by three-dimensional scanner 200. Identification device 100 includes: an input unit 1102 that receives the three-dimensional data; an identification unit 1130 that identifies a type of the tooth based on the three-dimensional data including a feature of the tooth received by input unit 1102 and an estimation model 114 (a learned model 114*a*) including a neural network 1142; and an output unit 1103 that outputs an identification result obtained by identification unit 1130. Estimation model 114 is learned based on: tooth information corresponding to the type of the tooth associated with the three-dimensional data; and the identification result about the type of the tooth that is obtained using the three-dimensional data.

Accordingly, user 1 inputs the three-dimensional data including data of a tooth into estimation model 114 (learned model 114*a*) including neural network 1142, and thus, can identify a type of the tooth, thereby allowing more accurate identification of a type of a tooth than in the case where a type of a tooth is identified depending on the user's knowledge.

An identification method includes: receiving three-dimensional data including data of the tooth (S48, S50); identifying a type of the tooth based on the three-dimensional data including a feature of the tooth and an estimation model 114 including a neural network 1142 (S52); and outputting an identification result obtained by the identifying a type of the tooth (S54). Estimation model 114 is learned based on the tooth information corresponding to the type of the tooth associated with the three-dimensional data and the identification result about the type of the tooth that is obtained using the three-dimensional data.

Accordingly, user 1 inputs the three-dimensional data including data of a tooth into estimation model 114 (learned model 114*a*) including neural network 1142, and thus can identify a type of the tooth, thereby allowing more accurate identification of a type of a tooth than in the case where a type of a tooth is identified depending on the user's knowledge.

An identification program 120 causes a computing device 130 to: receive three-dimensional data including data of the tooth (S48, S50); identify a type of the tooth based on the three-dimensional data including a feature of the tooth and an estimation model 114 including a neural network 1142 (S52); and output an identification result obtained by the identifying a type of the tooth (S54). Estimation model 114 is learned based on the tooth information corresponding to the type of the tooth associated with the three-dimensional data and the identification result about the type of the tooth that is obtained using the three-dimensional data.

Accordingly, user 1 inputs the three-dimensional data including data of a tooth into estimation model 114 (learned model 114*a*) including neural network 1142, and thus can identify a type of the tooth, thereby allowing more accurate identification of a type of a tooth than in the case where a type of a tooth is identified depending on the user's knowledge.

[Modifications]

The present invention is not limited to the above-described examples but is further variously modified and applied. The following describes modifications applicable to the present invention.

(Learning Process in Service Providing Process)

Figure 14:
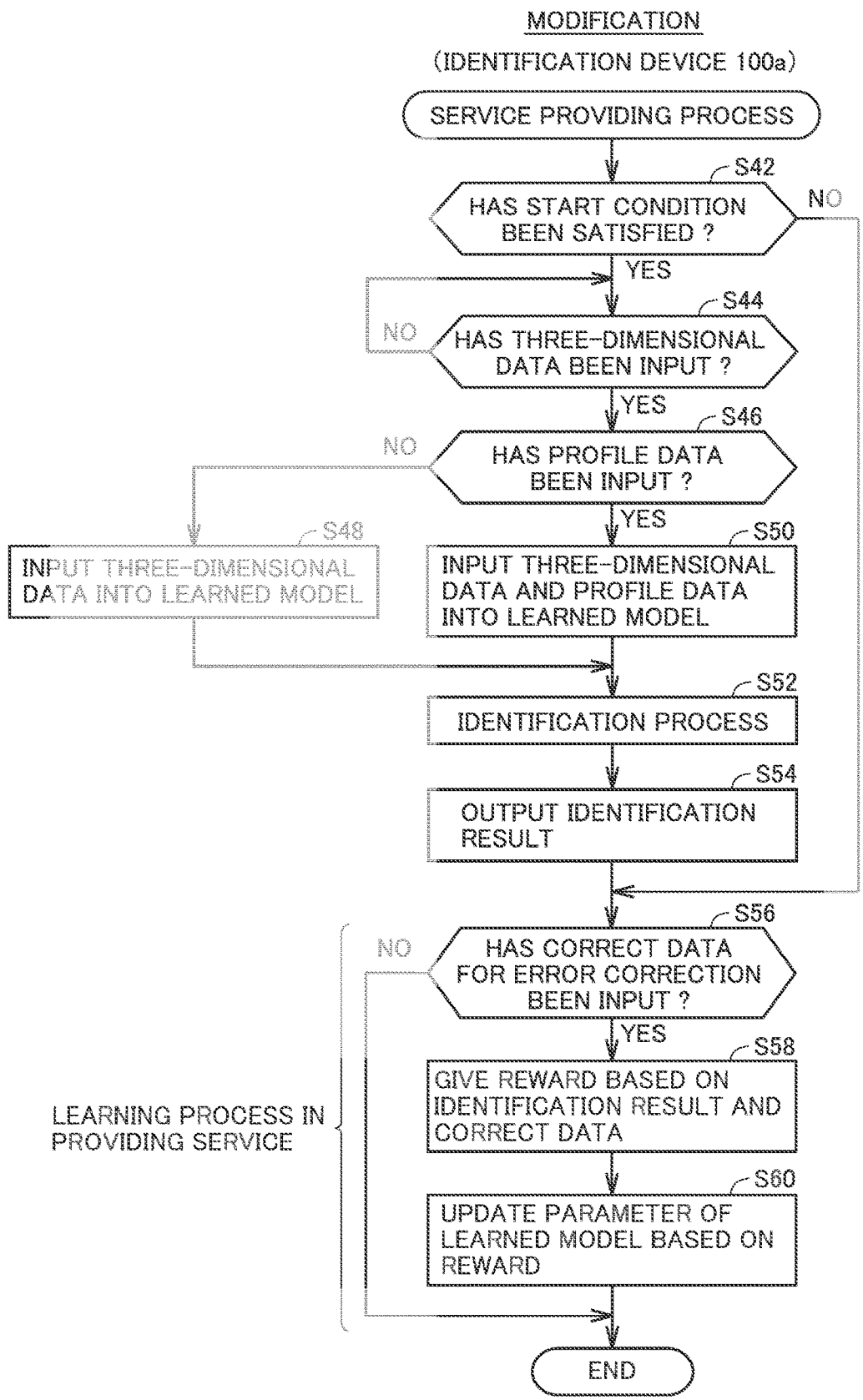
FIG. 14 is a flowchart for illustrating an example of a service providing process performed by an identification device according to a modification.

Although identification device 100 according to the present embodiment does not perform a learning process in the service providing process as shown in FIG. 13, an identification device 100*a* according to a modification may perform a learning process in the service providing process as shown in FIG. 14. FIG. 14 is a flowchart for illustrating an example of a service providing process performed by identification device 100*a* according to the modification. Since the processes in S42 to S54 shown in FIG. 14 are the same as the processes in S42 to S54 shown in FIG. 13, only the processes in and after S56 will be hereinafter described with reference to FIG. 14.

As shown in FIG. 14, identification device 100*a* outputs the identification result through the processes in S42 to S54, and then, performs a learning process in providing a service. Specifically, after S54, identification device 100*a* determines whether correct data for error correction has been input or not (S56). For example, when the type of the tooth that is the identification result output in S54 is different from the type of the tooth that is a target to be actually scanned, identification device 100*a* determines whether or not the error has been corrected by user 1 inputting the type of the tooth as a target to be actually scanned.

When the correct data for error correction has not been input (NO in S56), identification device 100*a* ends the process. On the other hand, when the correct data for error correction has been input (YES in S56), identification device 100*a* gives a reward based on the identification result and the correct data (S58).

For example, as the degree of dissociation between the identification result and the correct data is smaller, a minus point having a smaller value may be given as a reward. In contrast, as the degree of dissociation between the identification result and the correct data is larger, a minus point having a larger value may be given as a reward. Specifically, when a tooth for which the identification result is output is adjacent to a tooth for which the correct data is input, identification device 100*a* gives a minus point having a smaller value. In contrast, when a tooth for which the identification result is output is away from a tooth for which the correct data is input, identification device 100*a* gives a minus point having a larger value. In this way, identification device 100*a* gives a reward that varies in value depending on the degree of dissociation between the identification result and the correct data. The reward is not limited to a minus point but may be a plus point.

Identification device 100*a* updates parameter 1144 of learned model 114*a* based on the given reward (S60). For example, identification device 100*a* updates parameter 1144 of learned model 114*a* such that the minus point given as a reward approaches zero. Then, identification device 100*a* ends the present process.

In this way, identification device 100*a* according to the modification performs the learning process also in the service providing process. Thus, as the use frequency by user 1 is higher, the accuracy of the identification process is more improved, thereby allowing more accurate identification of a type of a tooth.

(Generation of Learned Model for Each Category)

Figure 15:
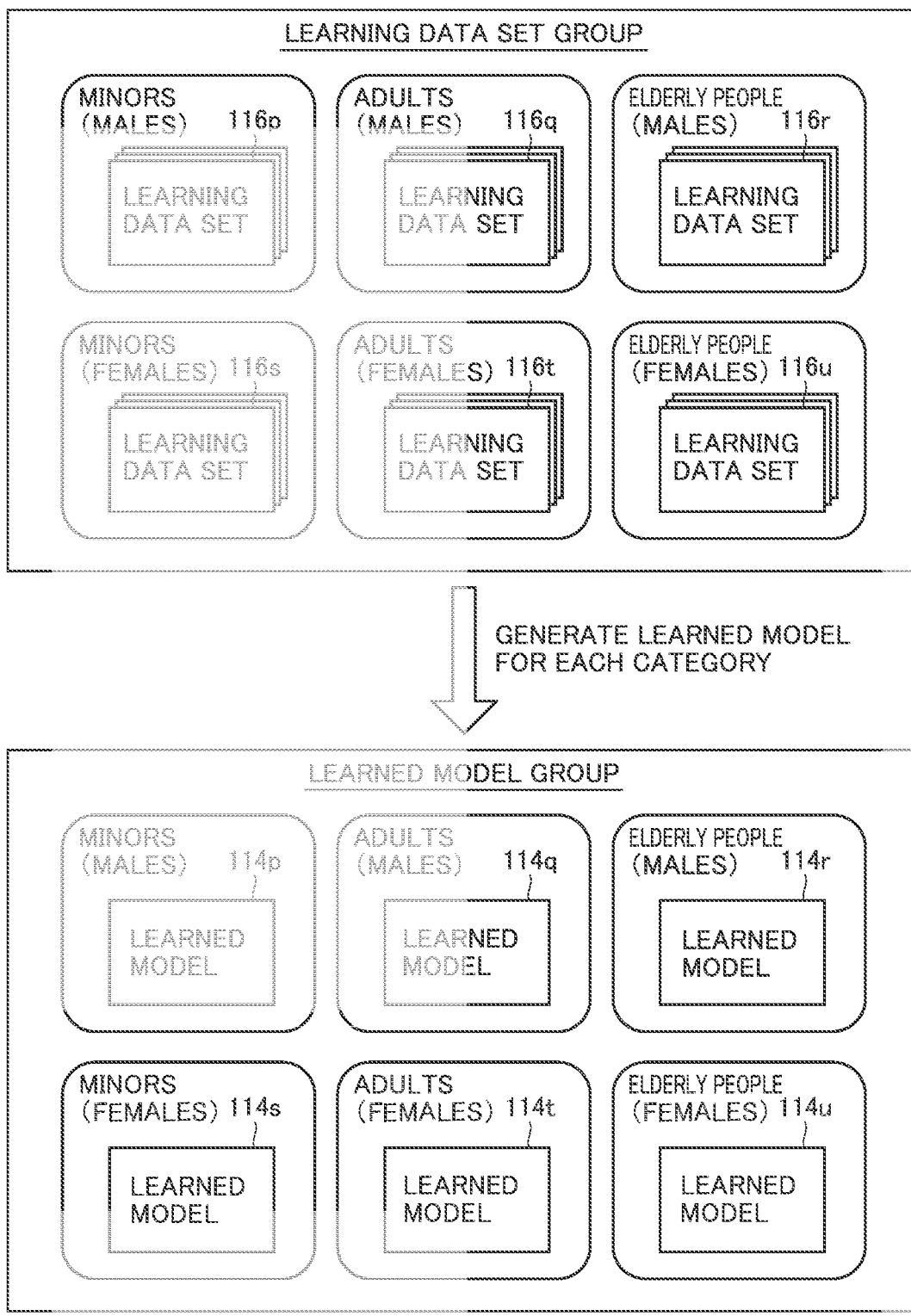
FIG. 15 is a schematic diagram for illustrating generation of a learned model based on a learning data set according to the modification.

Identification device 100 according to the present embodiment generates one learned model 114*a* by learning of estimation model 114 using a learning data set group including a plurality of learning data sets 116a to 116o classified for each category, as shown in FIG. 10. On the other hand, as shown in FIG. 15, an identification device 100b according to a modification may generate a learned model for each category by learning of estimation model 114 using a plurality of data sets, which are classified into categories, for each category. FIG. 15 is a schematic diagram for illustrating generation of a learned model based on a learning data set according to the modification.

As shown in FIG. 15, learning data set 116 is classified and held for each category based on the profile of subject 2 as a target to be scanned when learning data set 116 is generated. For example, learning data sets are assigned to six categories based on ages (minors, adults, elderly people) and genders (males, females).

Identification device 100b generates learned models 114p to 114u for each category by learning of estimation model 114 using respective learning data sets 116p to 116u, which are classified into categories, for each category.

In this way, identification device 100b according to the modification can generate the plurality of learned models 114p to 114u classified into categories. Thus, a type of a tooth can be identified more accurately by more detailed analysis according to the profile of subject 2.

It should be noted that generation of learned models 114p to 114u shown in FIG. 15 is also applicable to generation of learned model 514a held in server device 500. For example, learning data sets 116p to 116u shown in FIG. 15 may be applied to learning data set 516 held in server device 500, or learned models 114p to 114u shown in FIG. 15 may be applied to learned model 514a held in server device 500.

(Service Providing Process Using Learned Model for Each Category)

Figure 16:
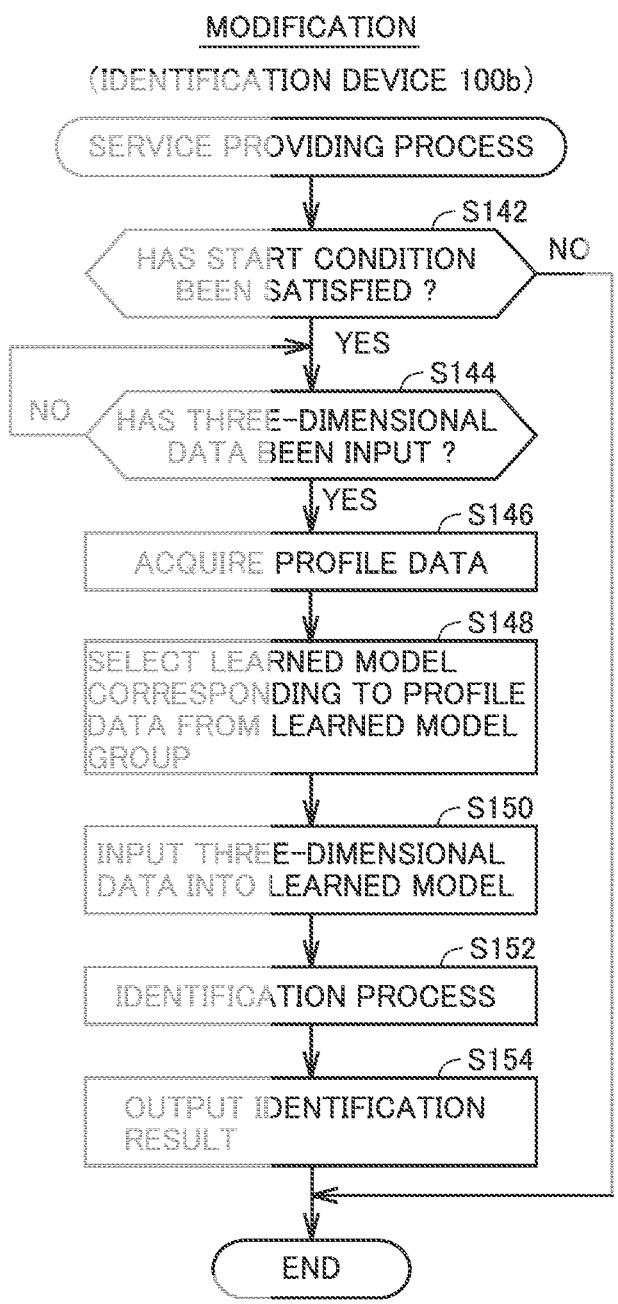
FIG. 16 is a flowchart for illustrating an example of a service providing process performed by an identification device according to a modification.

The service providing process performed by identification device 100 using learned models 114p to 114u for each category will be hereinafter described with reference to FIG. 16. FIG. 16 is a flowchart for illustrating an example of the service providing process performed by identification device 100b according to the modification. Each of steps shown in FIG. 16 is implemented by computing device 130 of identification device 100b executing OS 127 and identification program 120.

As shown in FIG. 16, identification device 100b determines whether a start condition for the service providing process has been satisfied or not (S142). Since the start condition is the same as the start condition shown in FIG. 13, the description thereof will not be repeated.

When the start condition has not been satisfied (NO in S142), identification device 100b ends the process. On the other hand, when the start condition has been satisfied (YES in S142), identification device 100b determines whether three-dimensional data has been acquired or not (S144). For example, identification device 100b determines whether a sufficient amount of three-dimensional data for performing the identification process has been acquired or not. When a sufficient amount of three-dimensional data has not been acquired (NO in S144), identification device 100b repeats the process in S144.

On the other hand, when a sufficient amount of three-dimensional data has been acquired (YES in S144), identification device 100b acquires profile data of subject 2 that is input by user 1 (S146). Then, identification device 100b selects a learned model corresponding to the profile data from a learned model group shown in FIG. 15 (S148). For example, when subject 2 is an elderly female, identification device 100b selects learned model 114u.

Then, identification device 100b inputs the three-dimensional data (position information) into the learned model (S150). Based on the feature of a tooth corresponding to the three-dimensional data, identification device 100b performs an identification process of identifying a type of the tooth using the learned model (S152).

Then, identification device 100b outputs the identification result obtained by the identification process to display 300, speaker 400, server device 500, and the like (S154), and then, ends the present process.

In this way, identification device 100b according to the modification can perform the identification process using a learned model most suitable to the profile of subject 2. Thus, a type of a tooth can be identified more accurately by more detailed analysis according to the profile of subject 2.

(Output of Profile)

Identification device 100 according to the present embodiment identifies a type of a tooth by the identification process. However, as shown in FIGS. 10 and 15, in view of the fact that the learned model is generated based on the learning data set obtained in consideration of the profile of subject 2, three-dimensional data may be input into the learned model in the identification process, and thereby, based on the feature of a tooth corresponding to the three-dimensional data, the profile of the owner of this tooth may be output as an identification result. In this way, the profile can be specified from the three-dimensional data including data of a tooth for an unidentified subject 2 found in a disaster event, a criminal event, or the like.

(Learning Process)

Identification device 100 according to the present embodiment updates parameter 1144 of estimation model 114 by the learning process, but does not necessarily have to update parameter 1144 and may update neural network 1142 by the learning process (for example, may update the algorithm of neural network 1142). Further, server device 500 according to the present embodiment updates the parameter of estimation model 514 by the learning process, but does not necessarily have to update the parameter and may update the neural network by the learning process (for example, may update the algorithm of the neural network).

(Identification with Normal Line and/or Color Information)

FIG. 17 is a schematic diagram for illustrating an example of a learning data set according to the modification. In addition to the position information included in the three-dimensional data acquired by three-dimensional scanner 200, an identification device 100c according to the modification may input actual color information of a tooth to estimation model 114, and thereby may learn estimation model 114.

For example, as described with reference to FIG. 9, the learning data set includes: position information that is data input into estimation model 114; and color-coded color information associated with a type of a tooth that is correct data, but may additionally include color information of a tooth before color-coding, as shown in FIG. 17. In the learning process, in addition to the position information, the color information of a tooth before color-coding is input into estimation model 114, so that learned model 114a may be generated also in consideration of the actual color information of the tooth.

Further, in addition to the position information as data input into estimation model 114 and the color-coded color information associated with the type of the tooth as correct data, the learning data set may include normal line information that can be calculated based on the position information, as shown in FIG. 17. In the learning process, in addition to the position information, the normal line information is input into estimation model 114, so that learned model 114a may be generated also in consideration of the normal line information.

The normal line information can be calculated in the following manner, for example. For example, with reference to one focused point among a plurality of points forming a tooth, a normal line to this one focused point is generated based on a plurality of points belonging to a prescribed range in the vicinity of the one focused point. Specifically, the normal line to the one focused point can be generated using the principal component analysis for a plurality of points belonging to a prescribed range in the vicinity of this one focused point. The principal component analysis can generally be performed by calculating a variance-covariance matrix. In the calculation of the variance-covariance matrix, characteristic vectors may be calculated to generate a principal component direction as a normal line to the one focused point. Since a method of generating a normal line to a point in a group of points is known, another commonly-known technique may be used.

In this way, the normal line information is added to the learning data set. Thereby, with reference to a plurality of points forming a tooth, the identification device can learn which side of the tooth formed by these points is a front surface. In addition, the identification device can learn the feature of a shape such as a recess based only on a group of a small number of points belonging to a prescribed range in the vicinity of the focused point.

The learning data set may include both the color information about a tooth before color-coding and the normal line information, or may include only one of the color information and the normal line information.

Figure 18:
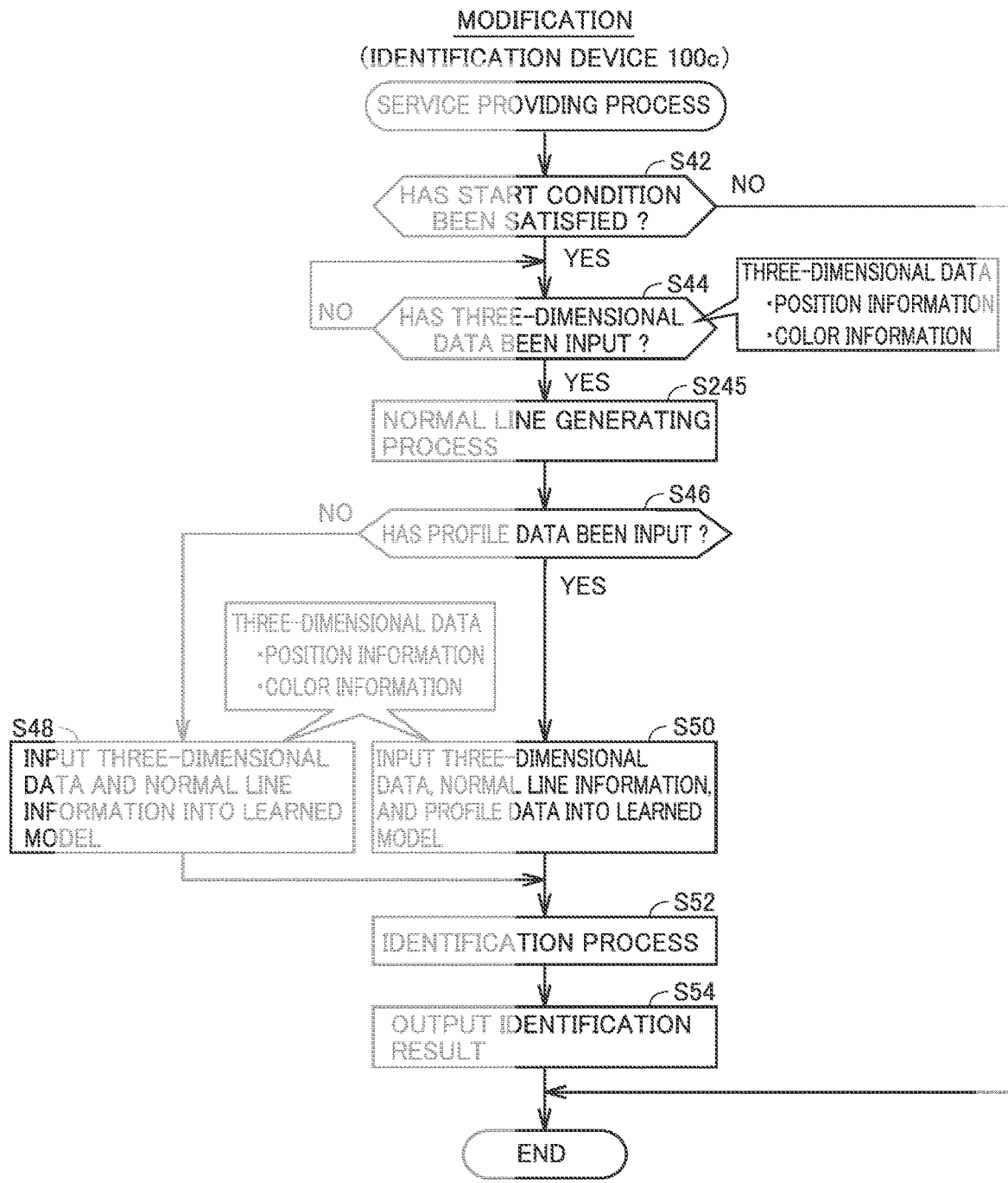
FIG. 18 is a flowchart for illustrating an example of a service providing process performed by an identification device according to a modification.

Then, referring to FIG. 18, the following describes a service providing process of performing an identification process using a learned model that is learned based on a learning data set including the color information about a tooth before color-coding and the normal line information. FIG. 18 is a flowchart for illustrating an example of the service providing process performed by identification device 100c according to the modification.

As shown in FIG. 18, identification device 100c according to the modification additionally performs the process in S245, unlike the service providing process performed by identification device 100 shown in FIG. 13. In other words, after the three-dimensional data has been input (YES in S44), identification device 100c generates normal lines to a plurality of points forming a tooth based on the position information included in the input three-dimensional data (S245). The input three-dimensional data includes color information about a tooth before color-coding in addition to the position information.

Then, when identification device 100c determines that the profile data has not been input (NO in S46), it inputs the normal line information to learned model 114a (S248), in addition to the three-dimensional data (position information, color information). On the other hand, when identification device 100c determines that the profile data has been input (YES in S46), it inputs the normal line information to learned model 114a, in addition to the three-dimensional data (position information, color information) and the profile data (S250). After S248 and S250, identification device 100c performs an identification process of identifying a type of a tooth using the learned model (S52).

In this way, identification device 100c according to the modification may identify a type of a tooth further based on: the color information of the tooth before color-coding; and the normal line generated for each of a plurality of points forming the tooth corresponding to the three-dimensional data. It should be noted that identification device 100c may receive the color information of a tooth before color-coding but may not receive the normal line information. Alternatively, identification device 100c may receive the normal line information but may not receive the color information about a tooth before color-coding.

In this way, identification device 100c can identify a type of a tooth based on the color information about the tooth before color-coding and/or the normal line generated for each of a plurality of points, thereby allowing more accurate identification of the type of the tooth.

It should be understood that the embodiments disclosed herein are illustrative and non-restrictive in every respect. The scope of the present invention is defined by the terms of the claims, rather than the description above, and is intended to include any modifications within the meaning and scope equivalent to the terms of the claims. The configuration described in the present embodiment and the configuration described in the modification can be combined with each other as appropriate.

REFERENCE SIGNS LIST

1 user, 2 subject, 5 network, 10 scanner system, 100, 100a, 100b identification device, 102 scanner interface 103, 503 display interface, 104 speaker interface, 105, 505 peripheral interface, 106, 506 network controller, 107, 507 medium reading device, 108 PC display, 109, 509 memory, 110, 510 storage, 112, 512 scan information, 114, 514 estimation model, 114a, 514a learned model, 116, 516 learning data set, 118, 518 color classification data, 119, 519 profile data, 120 identification program, 121, 521 learning program, 122, 522 three-dimensional data, 124, 524 identification result, 127, 527 OS, 130, 530 computing device, 200 three-dimensional scanner, 300, 350 display, 400 speaker, 500 server device, 550 removable disk, 601, 651 keyboard, 602, 652 mouse, 1102 input unit, 1103 output unit, 1119 profile acquisition unit, 1130 identification unit, 1142 neural network, 1144 parameter.

The invention claimed is:

1. An identification device that identifies a type of a tooth, the identification device comprising:
   an input unit that receives three-dimensional data including data of the tooth;
   an identification unit that identifies a type of the tooth based on
      the three-dimensional data including a feature of the tooth received by the input unit, and
      an estimation model including a neural network; and
   an output unit that outputs an identification result obtained by the identification unit,
   wherein
   in a case where the tooth corresponding to the three-dimensional data received by the input unit is an incisor in an upper jaw, a three-dimensional image corresponding to the three-dimensional data includes at least: an image of an area on an upper lip side; an image of an area on a palate side; and an image of an area on an incisal edge side,
   in a case where the tooth corresponding to the three-dimensional data received by the input unit is each of a canine and a molar in the upper jaw, the three-dimensional image corresponding to the three-dimensional data includes at least: an image of an area on a buccal side, an image of an area on a palate side, and an image of an occlusion area, in a case where the tooth corresponding to the three-dimensional data received by the input unit is an incisor in a lower jaw, the three-dimensional image corresponding to the three-dimensional data includes at least: an image of an area on a lower lip side, an image of an area on a tongue side, and an image of an area on the incisal edge side, and in a case where the tooth corresponding to the three-dimensional data received by the input unit is each of a canine and a molar in the lower jaw, the three-dimensional image corresponding to the three-dimensional data includes at least: an image of an area on the buccal side; an image of an area on the tongue side; and an image of the occlusion area.

2. The identification device according to claim 1, wherein the estimation model is learned based on tooth information corresponding to a type of the tooth associated with the three-dimensional data, and the identification result including the type of the tooth that is obtained using the three-dimensional data.

3. The identification device according to claim 1, wherein the input unit receives at least the three-dimensional data corresponding to a plurality of teeth adjacent to the tooth and gums in an oral cavity, and the identification unit identifies a type of each of the teeth based on the three-dimensional data including a feature of each of the teeth.

4. The identification device according to claim 1, wherein the three-dimensional data includes three-dimensional position information at each of a plurality of points forming the tooth corresponding to the three-dimensional data.

5. The identification device according to claim 4, wherein the position information includes coordinates of an absolute position based on a predetermined position.

6. The identification device according to claim 1, wherein a type of the tooth is identified further based on a normal line generated for each of a plurality of points forming the tooth corresponding to the three-dimensional data.

7. The identification device according to claim 1, wherein the output unit outputs the identification result to a display unit, and the display unit shows at least one of an image, a character, a numeral, an icon, and a symbol that correspond to the identification result.

8. The identification device according to claim 1, wherein the output unit outputs the identification result to an audio output unit, and the audio output unit outputs a sound corresponding to the identification result.

9. The identification device according to claim 1, wherein the output unit outputs the identification result to a server device, and the server device stores an accumulation of the identification result.

10. The identification device according to claim 2, wherein the estimation model includes at least one of a weighting factor and a determination value as a parameter used by the neural network, and the estimation model is learned by updating the parameter based on the tooth information and the identification result.

11. The identification device according to claim 2, wherein the tooth information includes at least one piece of information of a color, a character, a numeral, and a symbol that are associated with a type of the tooth corresponding to the three-dimensional data.

12. The identification device according to claim 2, wherein the tooth information is associated with the three-dimensional data to allow a range of each of a plurality of the teeth corresponding to the three-dimensional data to be specified.

13. The identification device according to claim 2, wherein the tooth information is associated with each of a plurality of points forming the tooth corresponding to the three-dimensional data.

14. The identification device according to claim 2, wherein the estimation model is learned based on attribute information related to a subject having the teeth, in addition to the tooth information and the identification result.

15. The identification device according to claim 14, wherein the attribute information includes at least one piece of information of an age, a gender, a race, a height, a weight, and a place of residence about the subject.

16. A scanner system that acquires shape information about a tooth, the scanner system comprising:

a three-dimensional scanner that acquires three-dimensional data including data of the tooth using a three-dimensional camera; and an identification device that identifies a type of the tooth based on the three-dimensional data including a feature of the tooth acquired by the three-dimensional scanner, wherein the identification device includes an input unit that receives the three-dimensional data, an identification unit that identifies a type of the tooth based on the three-dimensional data including a feature of the tooth received by the input unit, and an estimation model including a neural network, and an output unit that outputs an identification result obtained by the identification unit, wherein in a case where the tooth corresponding to the three-dimensional data received by the input unit is an incisor in an upper jaw, a three-dimensional image corresponding to the three-dimensional data includes at least: an image of an area on an upper lip side; an image of an area on a palate side; and an image of an area on an incisal edge side, in a case where the tooth corresponding to the three-dimensional data received by the input unit is each of a canine and a molar in the upper jaw, the three-dimensional image corresponding to the three-dimensional data includes at least: an image of an area on a buccal side, an image of an area on a palate side, and an image of an occlusion area, in a case where the tooth corresponding to the three-dimensional data received by the input unit is an incisor in a lower jaw, the three-dimensional image corresponding to the three-dimensional data includes at least: an image of an area on a lower lip side, an image of an area on a tongue side, and an image of an area on the incisal edge side, and in a case where the tooth corresponding to the three-dimensional data received by the input unit is each of a canine and a molar in the lower jaw, the three-dimensional image corresponding to the three-dimensional data includes at least: an image of an area on the buccal side; an image of an area on the tongue side; and an image of the occlusion area.

17. An identification method of identifying a type of a tooth, the identification method comprising:
  receiving three-dimensional data including data of the tooth;
  identifying a type of the tooth based on
    the three-dimensional data including a feature of the tooth, and
    an estimation model including a neural network; and
  outputting an identification result obtained by the identifying a type of the tooth,
  wherein
  in a case where the tooth corresponding to the three-dimensional data received by the input unit is an incisor in an upper jaw, a three-dimensional image corresponding to the three-dimensional data includes at least: an image of an area on an upper lip side; an image of an area on a palate side; and an image of an area on an incisal edge side,
  in a case where the tooth corresponding to the three-dimensional data received by the input unit is each of a canine and a molar in the upper jaw, the three-dimensional image corresponding to the three-dimensional data includes at least: an image of an area on a buccal side, an image of an area on a palate side, and an image of an occlusion area,
  in a case where the tooth corresponding to the three-dimensional data received by the input unit is an incisor in a lower jaw, the three-dimensional image corresponding to the three-dimensional data includes at least: an image of an area on a lower lip side, an image of an area on a tongue side, and an image of an area on the incisal edge side, and
  in a case where the tooth corresponding to the three-dimensional data received by the input unit is each of a canine and a molar in the lower jaw, the three-dimensional image corresponding to the three-dimensional data includes at least: an image of an area on the buccal side; an image of an area on the tongue side; and an image of the occlusion area.

* * * * *